(12) United States Patent
Cernasov et al.

(10) Patent No.: US 10,531,996 B2
(45) Date of Patent: Jan. 14, 2020

(54) SUPPORTING SURFACE WITH PROGRAMMABLE SUPPORTS AND METHOD TO REDUCE PRESSURE ON SELECTED AREAS OF A BODY

(71) Applicants: Andrei Cernasov, Ringwood, NJ (US); Nathalie Cernasov, Ringwood, NJ (US); Andre Cernasov, Ringwood, NJ (US)

(72) Inventors: Andrei Cernasov, Ringwood, NJ (US); Nathalie Cernasov, Ringwood, NJ (US); Andre Cernasov, Ringwood, NJ (US)

(*) Notice: Subject to any disclaimer, the term of this patent is extended or adjusted under 35 U.S.C. 154(b) by 632 days.

(21) Appl. No.: 15/345,280

(22) Filed: Nov. 7, 2016

(65) Prior Publication Data

US 2017/0128297 A1    May 11, 2017

Related U.S. Application Data

(60) Provisional application No. 62/251,977, filed on Nov. 6, 2015.

(51) Int. Cl.
*A61G 7/057* (2006.01)

(52) U.S. Cl.
CPC ........ *A61G 7/0573* (2013.01); *A61G 2203/34* (2013.01); *A61G 2203/46* (2013.01)

(58) Field of Classification Search
CPC ............. A61G 7/0573; A61G 2203/34; A61G 2203/46; A61B 5/1036; A61B 5/447; A61B 5/6892; A61B 5/6891

USPC .......................................................... 702/138
See application file for complete search history.

(56) References Cited

U.S. PATENT DOCUMENTS

| | | |
|---|---|---|
| 3,428,973 A | 2/1969 | Hargest et al. |
| 4,163,297 A | 8/1979 | Neumark |
| 4,278,079 A | 7/1981 | Simhoni et al. |
| 4,347,633 A | 9/1982 | Gammons et al. |
| 4,425,676 A | 1/1984 | Crane |
| 4,472,847 A | 9/1984 | Gammons et al. |
| 4,605,582 A | 8/1986 | Sias et al. |
| 4,614,000 A | 9/1986 | Mayer |
| 4,673,605 A | 6/1987 | Sias et al. |
| 4,723,328 A | 2/1988 | Kato |
| 4,768,250 A | 9/1988 | Kato |
| 4,768,251 A | 9/1988 | Baskent |
| 4,788,730 A | 12/1988 | Bexton |
| 4,799,276 A | 1/1989 | Kadish |
| 4,825,488 A | 5/1989 | Bedford |
| 4,847,933 A | 7/1989 | Bedford |

(Continued)

OTHER PUBLICATIONS

Jason J. Liu, et al., "Bodypart Localization for Pressure Ulcer Prevention", IEEE, 2014, pp. 766-769.

(Continued)

*Primary Examiner* — Ricky Ngon
(74) *Attorney, Agent, or Firm* — Mannava & Kang, P.C.

(57) ABSTRACT

A system and method to reduce pressure on selected areas on a body include an array of programmable supports and at least one sensor to detect a physical property of the body. Each programmable support of the array of programmable supports includes an adjustable member and a mechanism to adjust the length of the adjustable member based on the detected physical property of the body.

20 Claims, 18 Drawing Sheets

(56) References Cited

U.S. PATENT DOCUMENTS

| | | |
|---|---|---|
| 4,864,671 A | 9/1989 | Evans |
| 4,866,800 A | 9/1989 | Bedford |
| 4,944,060 A | 7/1990 | Peery et al. |
| 4,945,588 A | 8/1990 | Cassidy et al. |
| 4,955,096 A | 9/1990 | Gilroy et al. |
| 5,008,965 A | 4/1991 | Vrzalik |
| 5,010,608 A | 4/1991 | Barnett et al. |
| 5,031,261 A | 7/1991 | Fenner, Sr. |
| 5,072,468 A | 12/1991 | Hagopian |
| 5,083,551 A | 1/1992 | Addison, Jr. |
| 5,201,780 A | 4/1993 | Dinsmoor, III et al. |
| 5,243,721 A | 9/1993 | Teasdale |
| 5,255,404 A | 10/1993 | Dinsmoor, III et al. |
| 5,303,436 A | 4/1994 | Dinsmoor, III et al. |
| 5,325,551 A | 7/1994 | Tappel et al. |
| 5,490,299 A | 2/1996 | Dinsmoor, III et al. |
| 5,511,260 A | 4/1996 | Dinsmoor, III et al. |
| 5,564,142 A | 10/1996 | Liu |
| 5,592,707 A | 1/1997 | Dinsmoor, III et al. |
| 5,652,987 A | 8/1997 | Fujita |
| 5,657,488 A | 8/1997 | Urelli |
| 5,737,788 A | 4/1998 | Castellino et al. |
| 5,815,864 A | 10/1998 | Sloop |
| 5,926,884 A | 7/1999 | Biggie et al. |
| 5,956,787 A | 9/1999 | James et al. |
| 5,960,497 A | 10/1999 | Castellino et al. |
| 6,065,166 A | 5/2000 | Sharrock et al. |
| 6,073,289 A | 6/2000 | Bolden et al. |
| 6,151,740 A | 11/2000 | Morimoto et al. |
| 6,260,221 B1 | 7/2001 | Grabell et al. |
| 6,341,395 B1 | 1/2002 | Chao |
| 6,367,106 B1 | 4/2002 | Gronsman |
| 6,442,780 B1 | 9/2002 | Phillips et al. |
| 6,557,937 B1 | 5/2003 | Shah et al. |
| 6,591,437 B1 | 7/2003 | Phillips |
| 6,676,215 B1 | 1/2004 | Shah et al. |
| 6,782,574 B2 | 8/2004 | Totton et al. |
| 6,823,549 B1 | 11/2004 | Hampton et al. |
| 6,829,797 B2 | 12/2004 | Partian |
| 6,857,151 B2 | 2/2005 | Jusiak et al. |
| 6,874,185 B1 | 4/2005 | Phillips et al. |
| 6,920,881 B2 | 7/2005 | Narula et al. |
| 6,968,585 B2 | 11/2005 | Shaw |
| 6,976,281 B2 | 12/2005 | Schunk et al. |
| 7,039,454 B1 | 5/2006 | Kaga et al. |
| 7,197,780 B2 | 4/2007 | Petric |
| 7,219,380 B2 | 5/2007 | Beck et al. |
| 7,287,289 B1 | 10/2007 | Hagopian |
| 7,296,315 B2 | 11/2007 | Totton et al. |
| 7,305,727 B2 | 12/2007 | Horlin |
| 7,378,975 B1 | 5/2008 | Smith et al. |
| 7,583,199 B2 | 9/2009 | Graebe, Jr. |
| 7,823,219 B2 | 11/2010 | Freund |
| 7,823,232 B2 | 11/2010 | Tinke et al. |
| 8,081,083 B2 | 12/2011 | Hinterlong |
| 8,407,833 B2 | 4/2013 | Sauter et al. |
| 8,531,307 B2 | 9/2013 | Lachenbruch |
| 8,675,059 B2 | 3/2014 | Johnson et al. |
| 8,719,980 B2 | 5/2014 | Chen |
| 8,840,573 B2 | 9/2014 | Neustaedter et al. |
| 8,850,646 B2 | 10/2014 | Stelter et al. |
| 8,898,842 B2 | 12/2014 | Dennis |
| 8,945,637 B2 | 2/2015 | Danhof |
| 9,226,863 B1* | 1/2016 | El-Messeiry ...... A61G 7/05769 |
| 9,848,712 B2* | 12/2017 | Main ................. A47C 31/12 |
| 2002/0032929 A1 | 3/2002 | Bolden et al. |
| 2006/0085919 A1* | 4/2006 | Kramer ............... A47C 27/082 |
| | | 5/713 |
| 2009/0000037 A1 | 1/2009 | Graebe, Jr. |
| 2009/0056030 A1 | 3/2009 | Bolden |
| 2010/0101026 A1* | 4/2010 | Papaioannou ........ A61G 7/0573 |
| | | 5/710 |
| 2010/0268121 A1* | 10/2010 | Kilborn ................ A61B 5/412 |
| | | 600/587 |
| 2011/0094040 A1 | 4/2011 | deGreef et al. |
| 2011/0190674 A1 | 8/2011 | Dahl et al. |
| 2011/0308019 A1* | 12/2011 | Terawaki ........... A61G 7/05769 |
| | | 5/713 |
| 2012/0277637 A1* | 11/2012 | Vandatpour ......... A47C 31/123 |
| | | 600/595 |
| 2012/0291204 A1 | 11/2012 | Takeda et al. |
| 2013/0019408 A1* | 1/2013 | Jacofsky ............. A47C 27/083 |
| | | 5/613 |
| 2013/0281804 A1* | 10/2013 | Lee ........................ A61B 5/447 |
| | | 600/324 |
| 2014/0039351 A1* | 2/2014 | Mix ...................... A61B 5/1114 |
| | | 600/587 |
| 2014/0208520 A1 | 7/2014 | Totton et al. |
| 2014/0259406 A1* | 9/2014 | Ead ..................... A47C 21/028 |
| | | 5/488 |
| 2014/0345058 A1 | 11/2014 | Escobedo et al. |
| 2015/0371522 A1* | 12/2015 | Mravyan ................ H04W 4/38 |
| | | 340/573.1 |
| 2016/0008206 A1* | 1/2016 | Devanaboyina ....... A47C 9/002 |
| | | 601/136 |
| 2016/0125716 A1* | 5/2016 | Ribble ............... G08B 21/0461 |
| | | 340/573.4 |
| 2016/0228050 A1* | 8/2016 | Sugla ................ A61G 7/05776 |
| 2016/0256100 A1* | 9/2016 | Jacofsky ............. A47C 31/123 |
| 2016/0350489 A1* | 12/2016 | Ribble .................. G06Q 50/24 |
| 2017/0000670 A1* | 1/2017 | Ead ....................... A61G 7/057 |
| 2017/0056263 A1* | 3/2017 | Ead ....................... A61G 7/057 |
| 2017/0325683 A1* | 11/2017 | Larson .................. G16H 50/30 |
| 2017/0348181 A1* | 12/2017 | Perriard .............. A43B 13/203 |

OTHER PUBLICATIONS

Zachary Brush, et al., "Design and Control of a Smart Bed for Pressure Ulcer Prevention", IEEE/ASME International Conference on Advanced Intelligent Mechatronics (AIM), Wollongong, Australia, Jul. 9-12, 2013, pp. 1033-1038.

C. Gehin, et al., "Which techniques to improve the early detection and prevention of pressure ulcers?", Proceedings of the 28th IEEE, EMBS Annual International Conference, New York City, USA, Aug. 30-Sep. 3, 2006, pp. 6057-6060.

Prabhu Jude Rajendran, et al., "Improving the Detection of Stage I Pressure Ulcers by Enhancing Digital Color Images", Proceedings of the 28th IEEE, EMBS Annual International Conference, New York City, USA, Aug. 30-Sep. 3, 2006, p. 5206-5209.

Jean-François Deprez, et al., "3D Ultrasound Elastography for Early Detection of Lesions. Evaluation on a Pressure Ulcer Mimicking Phantom.", Proceedings of the 29th Annual International Conference of the IEEE EMBS, Cité Internationale, Lyon, France, Aug. 23-26, 2007, p. 79-82.

Dimitrios I. Kosmopoulos, et al., "Automated Pressure Ulcer Lesion Diagnosis for Telemedicine Systems, Increasing Efficiency and Monitoring Capabilities for Large Volumes of Patient Data", IEEE Engineering in Medicine and Biology Magazine, Sep./Oct. 2007, p. 18-22.

Marshal S. Dhillon MS, et al., "Towards the Prevention of Pressure Ulcers with a Wearable Patient Posture Monitor Based on Adaptive Accelerometer Alignment", 34th Annual International Conference of the IEEE EMBS, San Diego, California USA, Aug. 28-Sep. 1, 2012, p. 4513-4516.

Sarah Ostadabbas, et al., "A Resource-Efficient Planning for Pressure Ulcer Prevention", IEEE Transactions on Information Technology in Biomedicine, vol. 16, No. 6, Nov. 2012, p. 1265-1273.

Sarah Ostadabbas, et al., "Pressure Ulcer Prevention: An Efficient Turning Schedule for Bed-Bound Patients", IEEE/NIH Life Science Systems and Applications Workshop (LiSSA), 2011, p. 159-162.

Nicholas Wettels, et al., "Biomimetic Tactile Sensor for Control of Grip", 9 pages. http://bme.usc.edu/assets/004/55219.pdf.

Nicholas Wettels, et al., "Biomimetic Tactile Sensor Array", Advanced Robotics 22, Koninklijke Brill NV, Leiden and The Robotics Society of Japan, 2008, p. 829-849.

Leaf Healthcare, Inc., "The next step in wireless patient monitoring", 2014, 2 pages.

Marcus Yip, et al., "A Flexible Pressure Monitoring System for Pressure Ulcer Prevention", 31st Annual International Conference

(56) References Cited

OTHER PUBLICATIONS of the IEEE EMBS, Minneapolis, Minnesota, USA, Sep. 2-6, 2009, p. 1212-1215.

Jalloul Elfehri, et al., "Novel approach of ulcer prevention based on pressure distribution control algorithm", Proceedings of the 2011 IEEE International Conference on Mechatronics and Automation, Aug. 7-10, Beijing, China, p. 265-270.

Inhyuk Moon, et al., "Control of Air-cell Mattress for Preventing Pressure Ulcer Based on Approximate Anthropometric Model", Proceedings of the 2005 IEEE, 9th International Conference on Rehabilitation Robotics, Jun. 28-Jul. 1, 2005, Chicago, IL, USA, p. 164-167.

Farve Daneshvar Fard, et al., "Pressure Ulcer Risk Assessment by Monitoring Interface Pressure and Temperature", IEEE, 2013.

Courtney H. Lyder, et al., "Chapter 12. Pressure Ulcers: A Patient Safety Issue", Patient Safety and Quality: An Evidence-Based Handbook for Nurses, Rockville, Maryland, Apr. 2008, 33 pages.

Royal College of Nursing, "The use of pressure-relieving devices (beds, mattresses and overlays) for the prevention of pressure ulcers in primary and secondary care", London, U.K., First published Oct. 2003, Reprinted Dec. 2004, 126 pages.

E. Mcinnes, et al., "Support surfaces for pressure ulcer prevention (Review)", published in The Cochrane Library 2011, Issue 4, 124 pages.

National Pressure Ulcer Adivosry Panel, Support Surface Sandards Initiative, "Terms and Definitions Related to Suppoert Surfaces", Ver. Jan. 29, 2007, 10 pages.

David R. Thomas, MD, "Prevention and treatment of pressure ulcers: What works? What doesn't?", Cleveland Clinic Journal of Medicine, vol. 68, No. 8, Aug. 2001, Downloaded from www.ccjm.org on Dec. 17, 2014, pp. 704-722.

European Pressure Ulcer Advisory Panel & National Pressure Ulcer Advisory Panel, "Prevention of Pressure Ulcers: Quick Reference Guide", 2009, 26 pages.

European Pressure Ulcer Advisory Panel & National Pressure Ulcer Advisory Panel, "Treatment of Pressure Ulcers: Quick Reference Guide", 2009, 47 pages.

\* cited by examiner

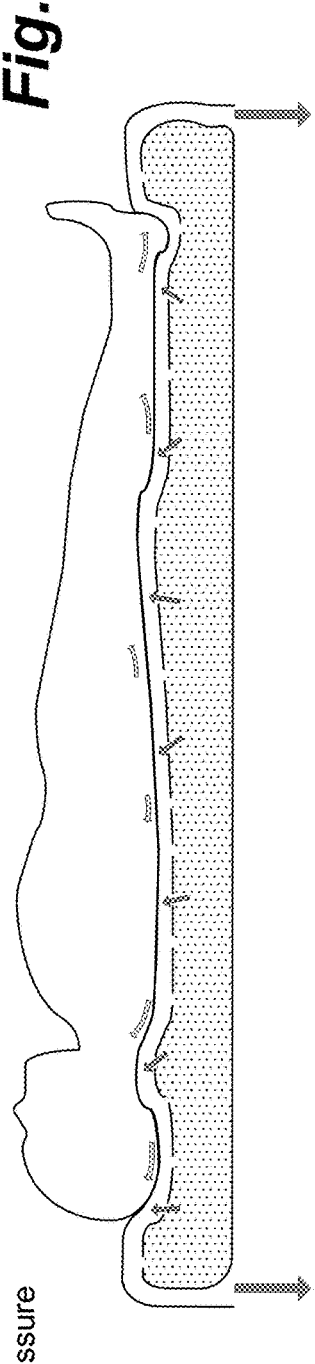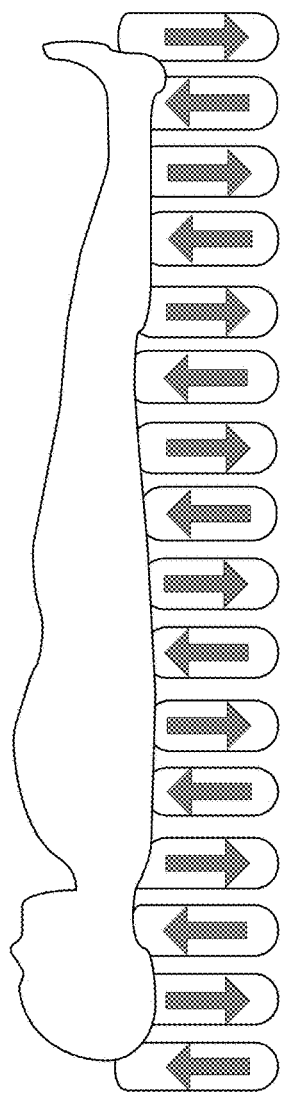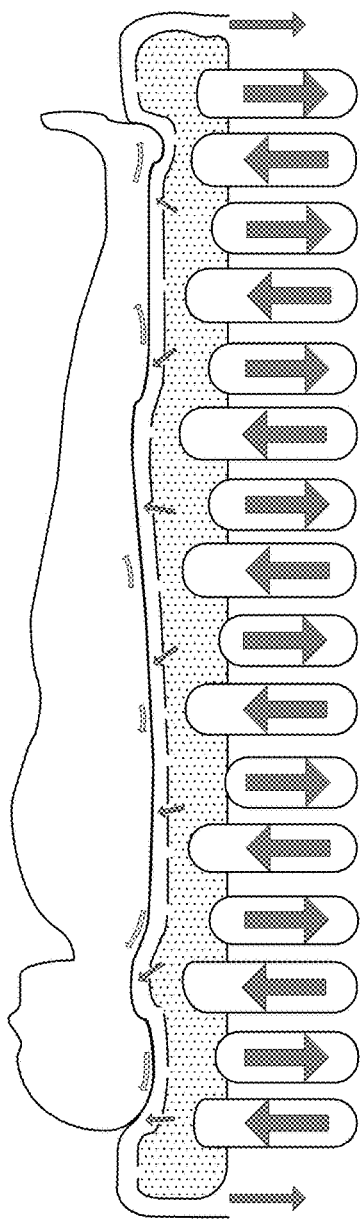

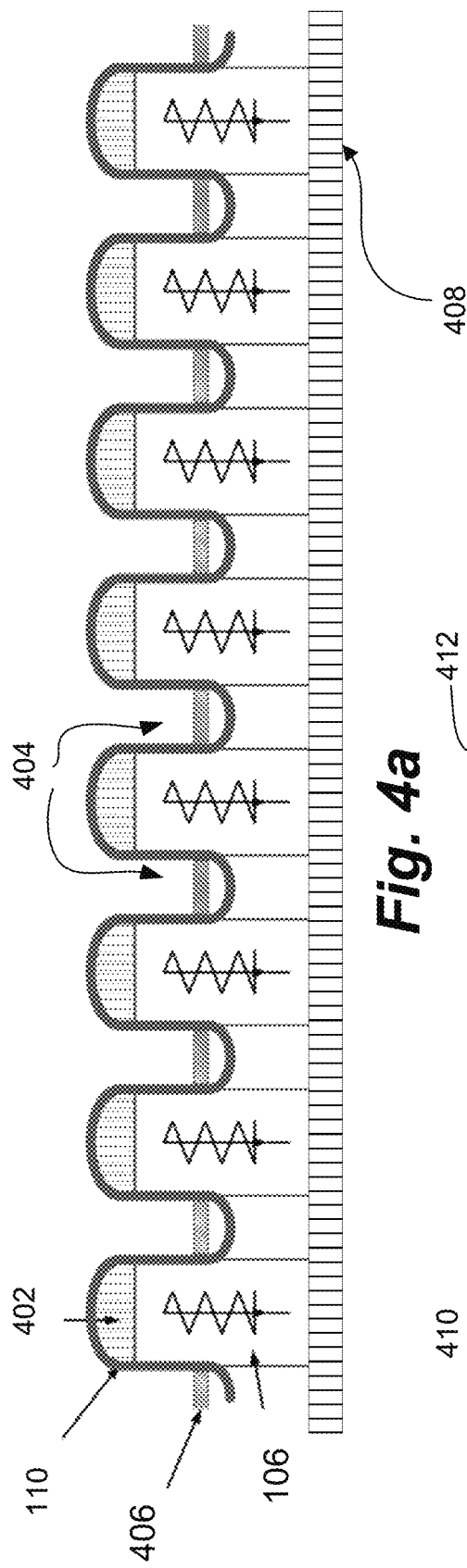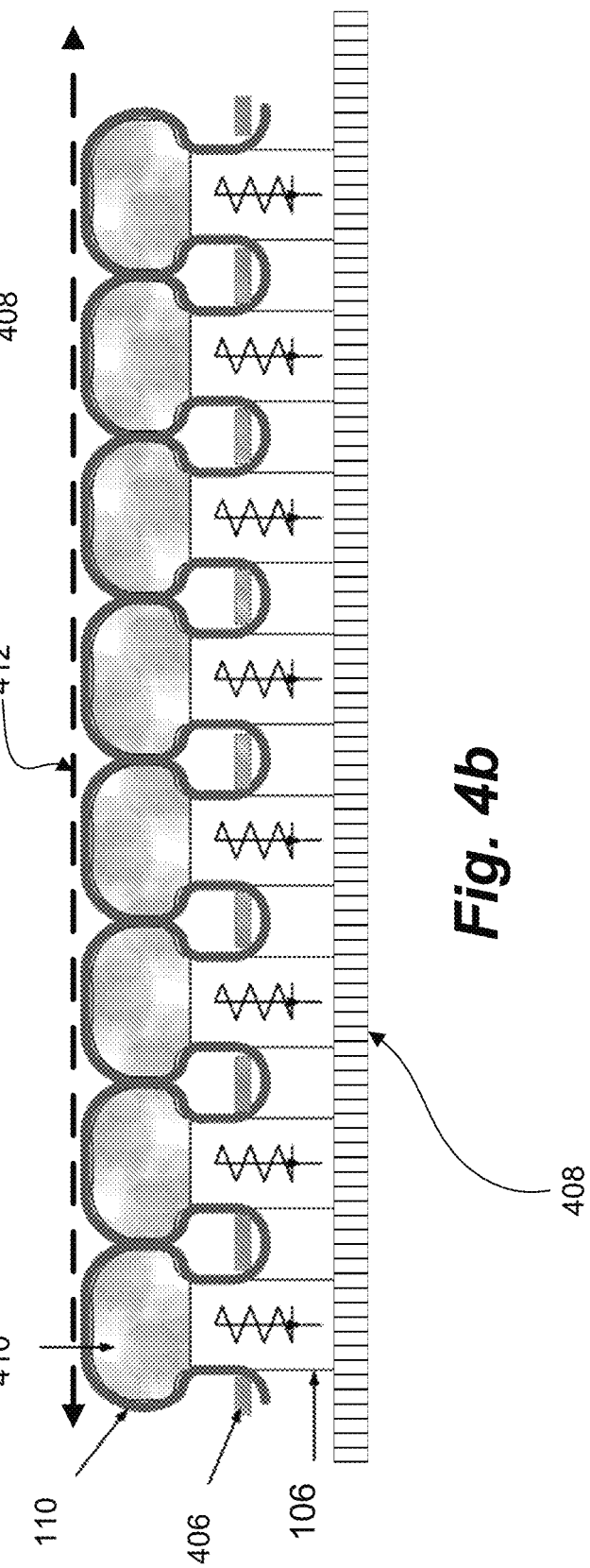
Fig. 4a
Fig. 4b

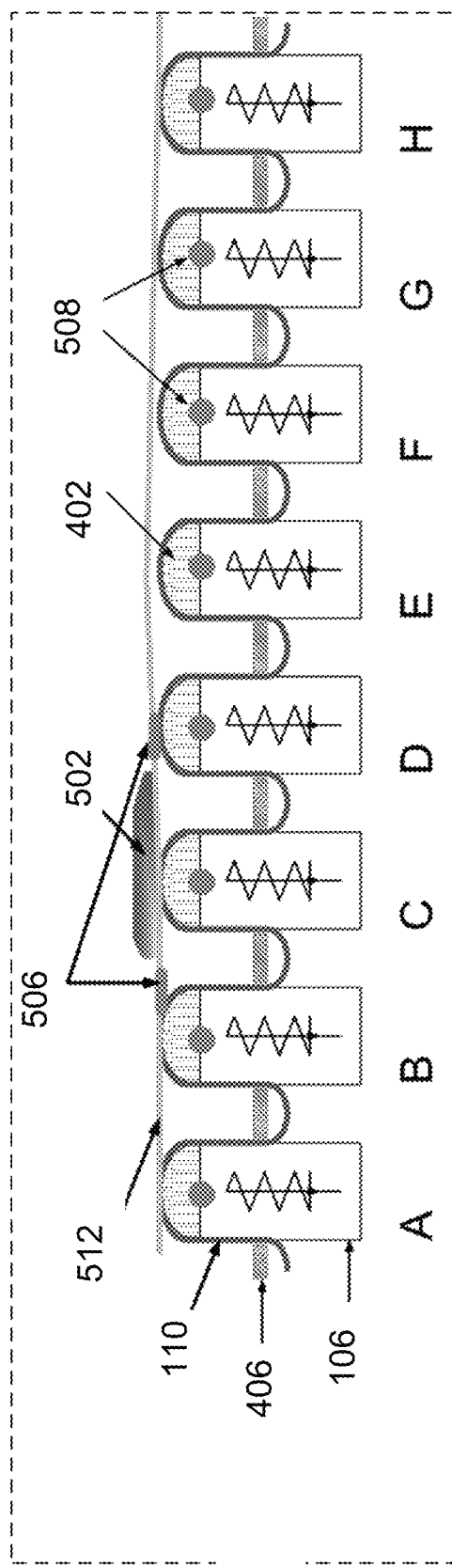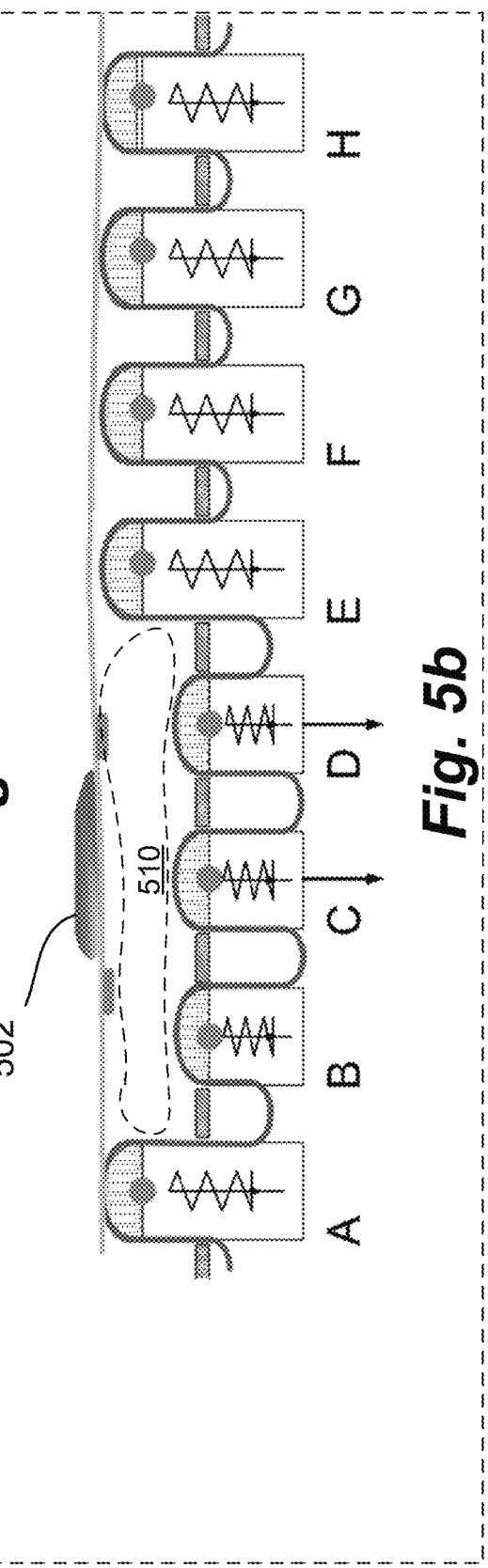

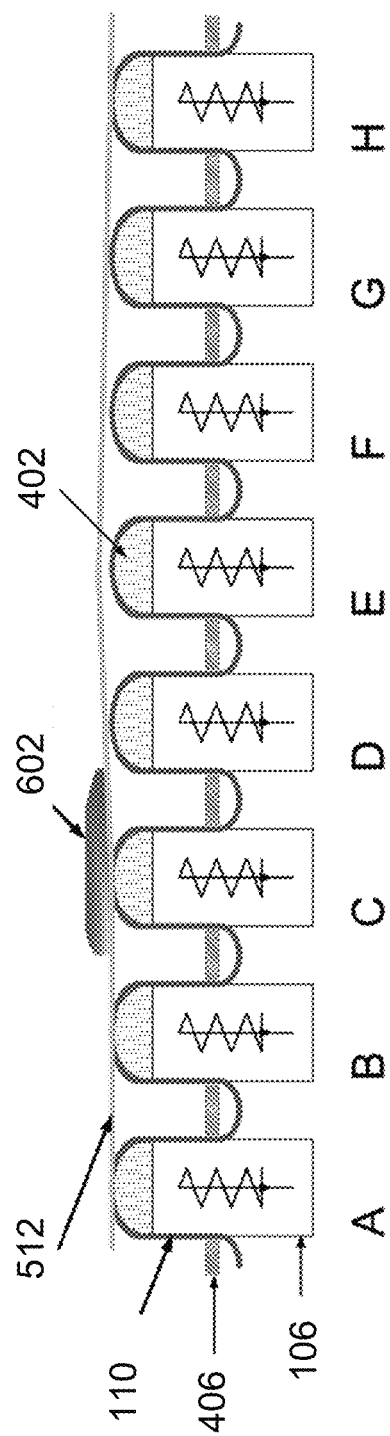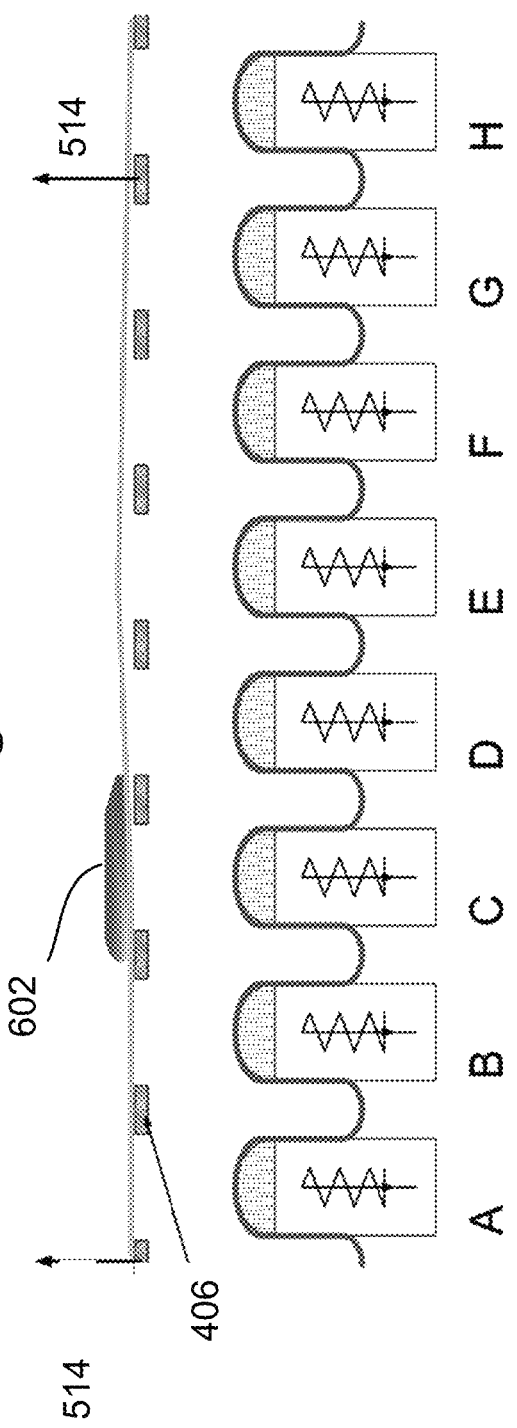

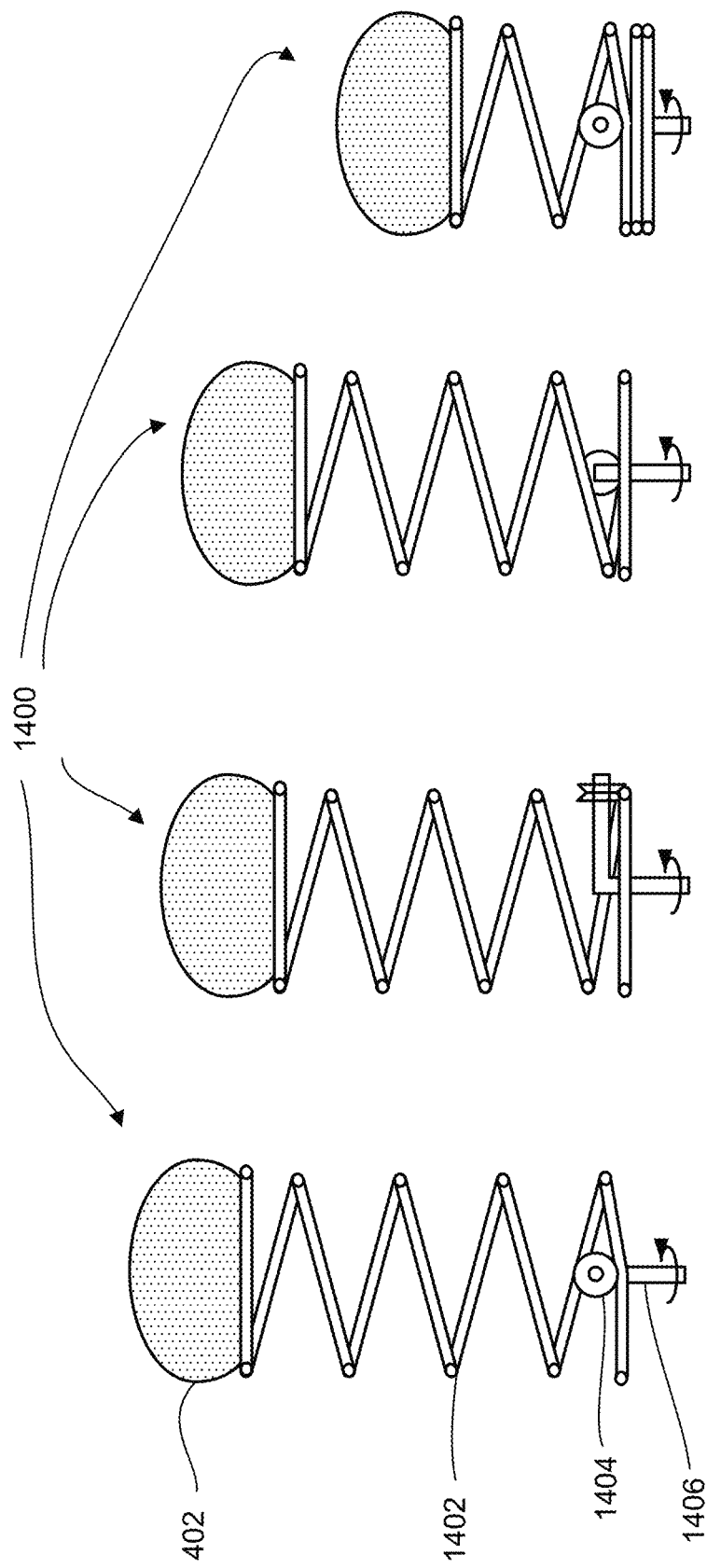

SUPPORTING SURFACE WITH PROGRAMMABLE SUPPORTS AND METHOD TO REDUCE PRESSURE ON SELECTED AREAS OF A BODY

CLAIM FOR PRIORITY

The present application claims priority to U.S. Provisional application No. 62/251,977, filed on Nov. 6, 2015, which is incorporated by reference herein in its entirety.

BACKGROUND

Localized areas of skin damage and adjacent tissues are often due to applied pressure, friction, or shear. These areas of skin damage include decubitus ulcers, which are also known as pressure sores, bedsores and pressure ulcers. These sores most often occur over bony prominences such as the hips, heels, spine, and other joints and are the result of a prolonged lack of blood flow to the affected area. Although the development of these sores is based on a variety of factors such as age, nutrition, skin moisture, and general health, pressure ulcers are usually found in patients suffering from immobility, spinal cord injury, or other severe illnesses and the elderly.

Annual costs of treating pressure ulcers in the US are in excess of three billion dollars. Prevention of pressure ulcers is of major importance to clinics, hospitals and nursing care facilities. Specialty beds are a major part of the solution. Most designs attempt to redistribute the pressure that builds up underneath body protrusions where ulcers tend to develop (buttocks, elbow, hips, heels, ankles, shoulders, back, and back of head).

FIGS. 2a-c depict existing beds to address pressure ulcers and include low air loss mattresses, alternating pressure mattresses, air fluidized beads mattresses or a combination of low air loss mattresses, alternating pressure mattresses, and air fluidized beads mattresses.

BRIEF DESCRIPTION OF DRAWINGS

The disclosed features are described in detail in the following description with reference to the following figures.

FIGS. 2a-c illustrate existing beds that address pressure distribution on the body.

FIGS. 4a and 4b illustrate one example of the programmable supports depicted in FIG. 1.

FIGS. 5a and 5b illustrate the operation of the programmable supports based upon markers and marker sensors according to examples of the present disclosure.

FIGS. 6a and 6b illustrate the operation of a lift sheet stretcher according to an example of the present disclosure.

FIGS. 14a-14d illustrate a programmable support that includes a roller mechanism according to an example of the present disclosure.

DETAILED DESCRIPTION

A supporting structure having an array of programmable supports, as described below, reduces pressure on selected areas of the body that are most likely to develop pressure ulcers, areas that are irritated, infected, have developed pressure ulcers, or are other areas of interest identified by a care giver. In examples a supporting surface with the described array of programmable supports protects an identified part of the body, while not affecting other parts of the body.

More specifically, described examples includes a support surface with an array of programmable supports that decrease pressure onto selected areas of the body while at the same time, allowing a minimal increase the pressure on the rest of the body. By allowing only a minimal increase in pressure on non-identified areas of the body, a risk of pressure ulceration in unexpected areas of the body may be minimized. Disclosed examples of support surfaces with an array of programmable supports map the pressure across a surface of the array of programmable supports, identify where the pressure is high enough to correspond to high risk points, and actively reduce the pressure at those points.

For simplicity and illustrative purposes, features are described by referring mainly to examples thereof. In the following description, numerous specific details are set forth in order to provide a thorough understanding of the features. It is apparent that the disclosed features may be practiced without limitation to all the specific details. Furthermore, the disclosed features may be used together in various combinations.

Figure 1:
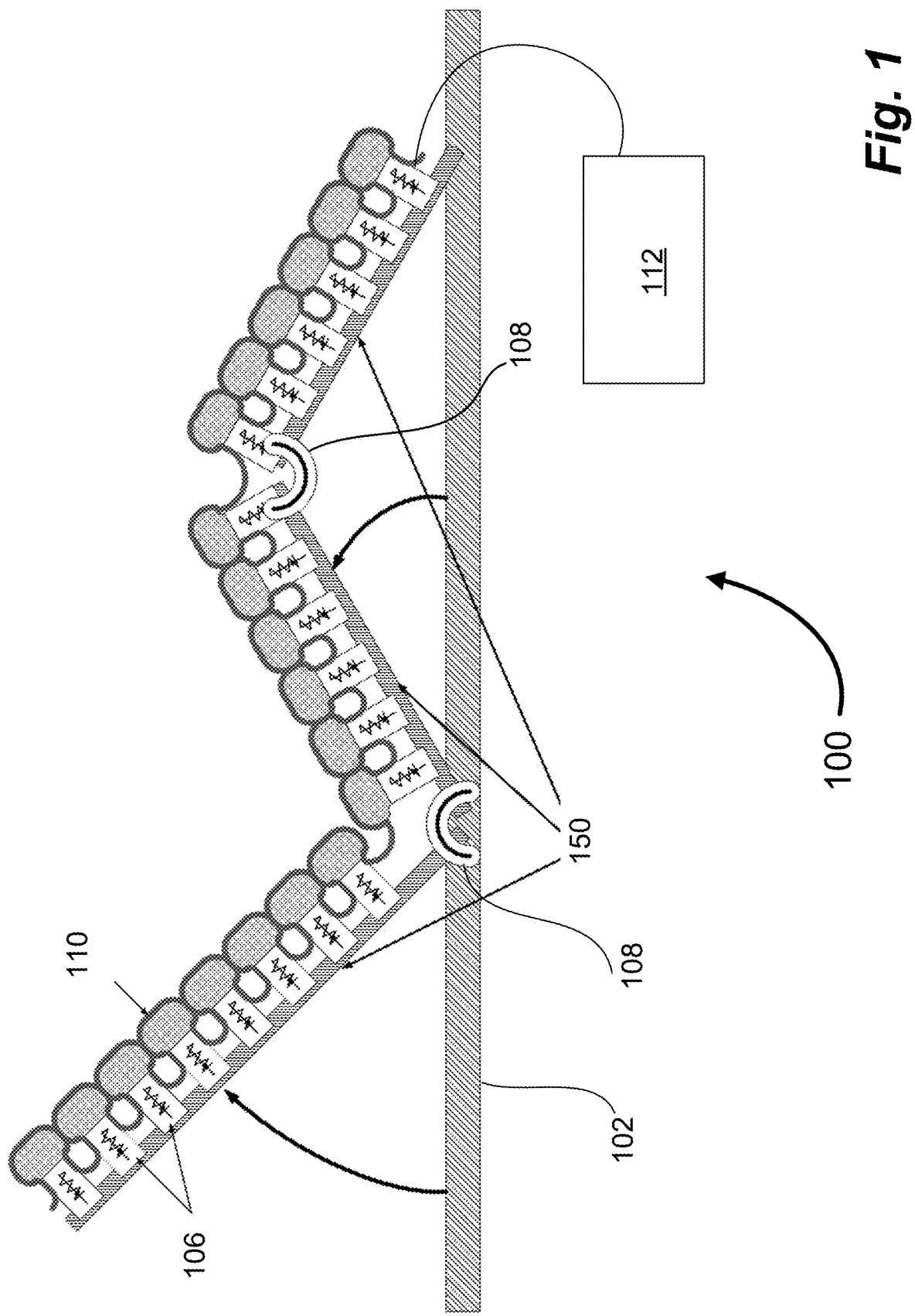
FIG. 1 illustrates a system to reduce pressure exerted on areas of interest of the body according to an example of the present disclosure.

FIG. 1 depicts an example of a system 100 that operates continually to reduce pressure on those parts of the body that are most likely to develop pressure ulcers. FIG. 1 depicts a general layout of a supporting surface 102 that includes three panels 104 in which a standard mattress or pad is replaced by an array of programmable supports 106, (a programmable support 106 may also be referred to hereinafter as "a support 106"), which can extend or contract under computer control to modify the pressure exerted locally on the skin by each of the supports 106. Support 106 includes an adjustable member, which in an example includes a spring, rod, air bubble, or other device operable to adjust its length in response to a control signal. FIG. 1 shows supports 106 disposed on panels 150 supported by a frame 108. A conformal cover sheet 110 is disposed on a top surface of the array of supports 106. A controller 112 is operable to monitor a position of a body resting on supports 106, and to adjust a length of each of the supports 106 based on a calculation.

Figure 3:
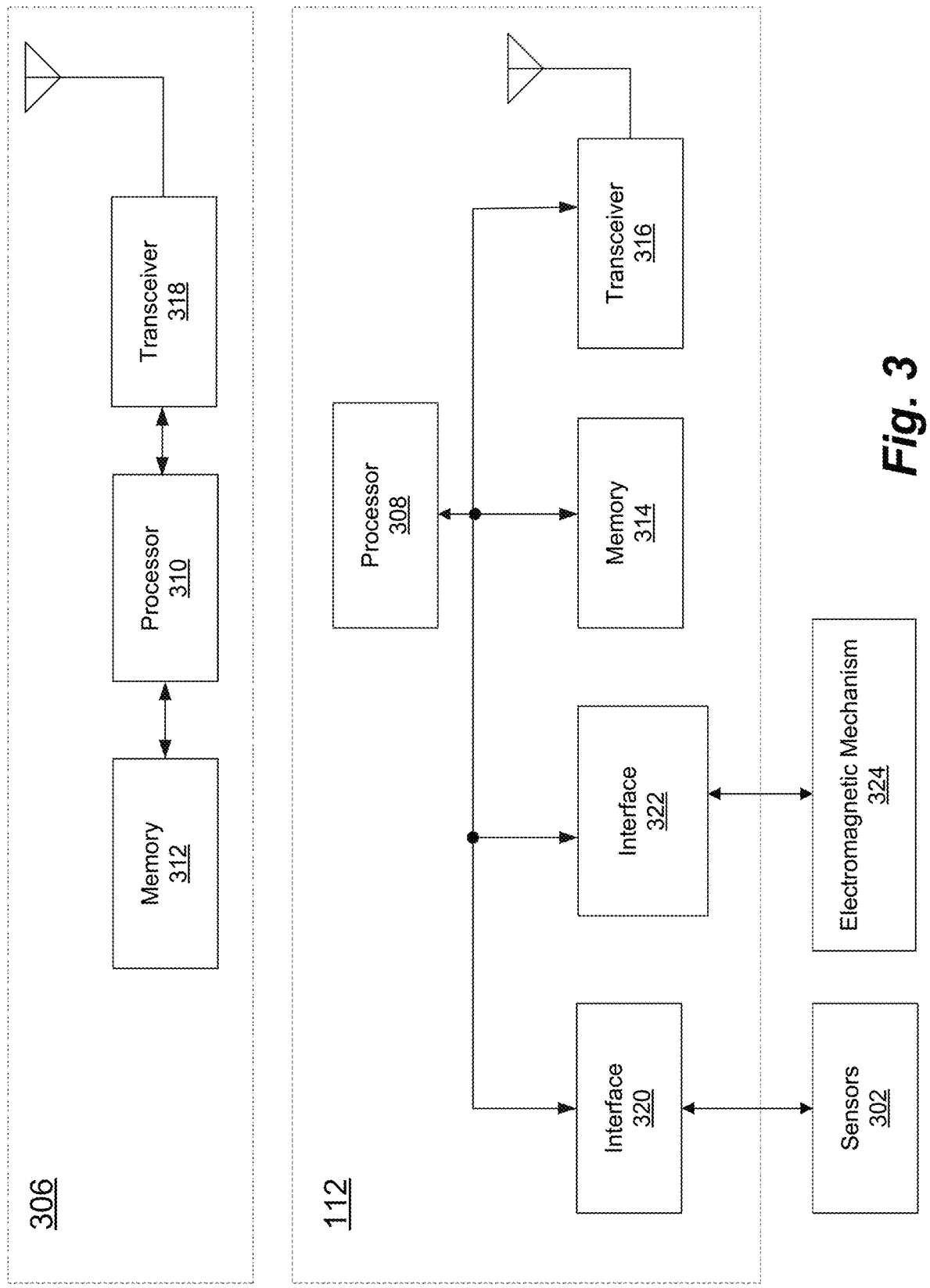
FIG. 3 illustrates a block diagram of a control mechanism of the system depicted in FIG. 1.

FIG. 3 depicts a block diagram of the controller 112 which operates to at least one of detect, monitor, and measure, a physical property of the body via sensors 302, at least one area of the body, identified by a caregiver, as to be protected. Controller 112 automatically adjusts, via an electro mechanic mechanism 324, an extension and contraction of each support 106. In an example, a single controller 112 controls a single array of supports 106 for a single support surface. In situations that include multiple arrays of supports 106, such as in a hospital ward with multiple beds, a controller 306 may be included to manage multiple arrays of supports 106 for a plurality of patients.

Figure 7:
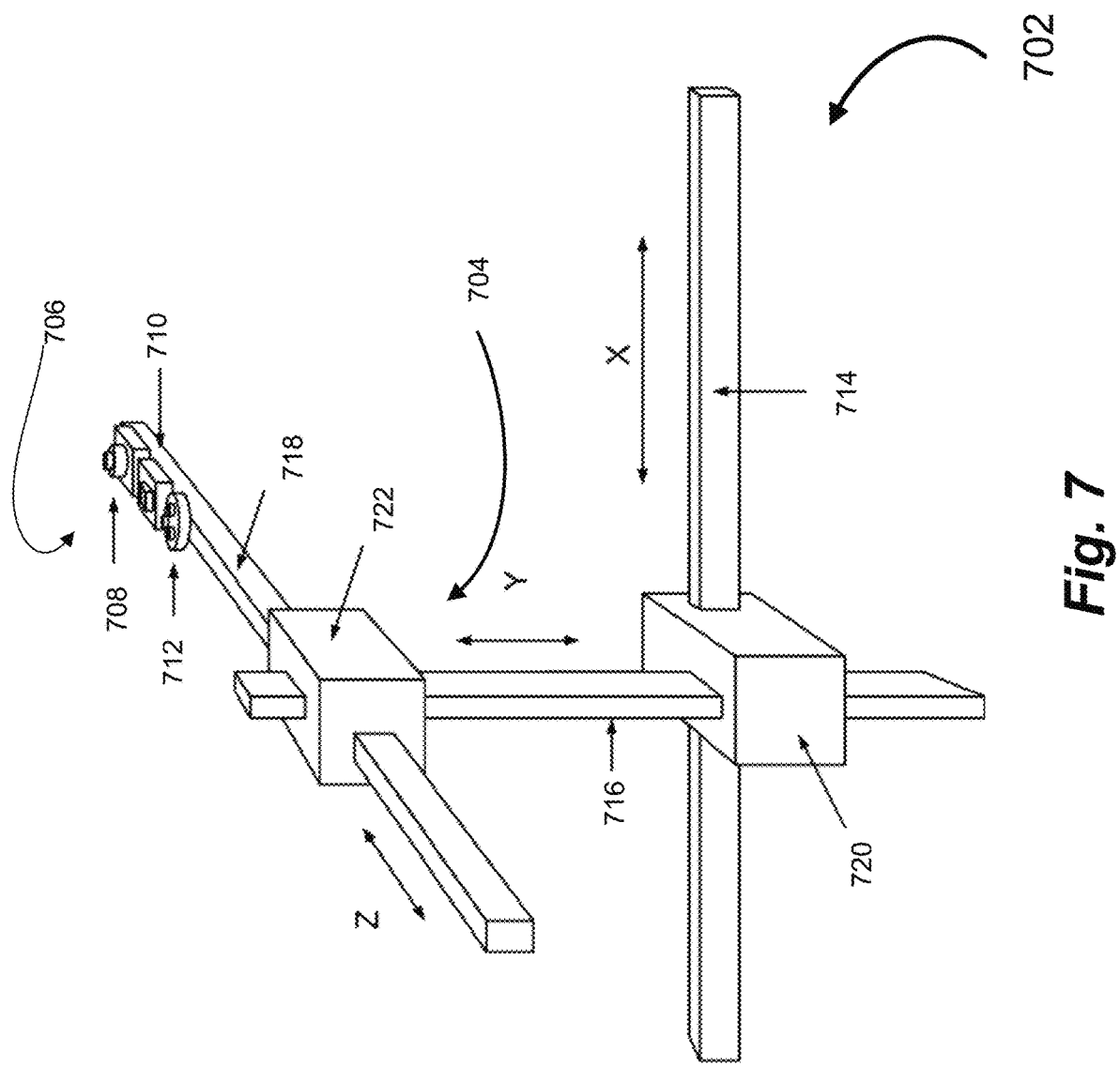
FIGS. 7-8 illustrate a mechanism to deliver sensors and/or actuators to determined locations of the skin surface according to an example of the present disclosure.

In examples, at least one of controllers 306 and 112 receives a signal from the at least one sensor 302. In an example, the at least one sensor 302 is disposed at a fixed position proximate to the at least one area of the body identified as to be protected. In another example, the at least one sensor 302 is mounted on a three-dimensional targeting assembly 702, as depicted in FIG. 7, and traverses beneath the body to detect a physical property of the body. The at least one controller determines a location of the at least one area based on the received signal from the at least one sensor 302, identifies at least one support 106 of the array of supports 106, proximate to the determined location of the at least one area; and provide a signal to a mechanism 914, corresponding to the determined at least one support 106. The signal is to cause the mechanism 914 to adjust the length of the determined at least one support 106.

In an example, controllers 112 and 306 include processors 308 and 310 and memory devices 312 and 314, respectively. Memory devices 312 and 314 are non-volatile local computer readable mediums to store program code executed by respective processors 308 and 310. Controllers 112 and 306 communicate via transceivers 316 and 318, and one controller may provide software updates and other information to the other controller.

Transceivers 316 and 318 communicate via a wired or wireless link based on radio frequency (RF), infrared (IR), acoustic, optic or other wireless communication technology including BLUETOOTH™ and Wi-Fi. The data transmission may be periodic, continuous, pushed to or pulled from processor 308 to processing 310.

In an example, controller 112 includes a sensor interface 320 to receive data from sensors 302. Sensors 302 detect at least one of position, movement, pressure, temperature, or other detectable conditions caused by a body in the vicinity of support 106. In examples, sensors 302 include pressure sensors, e.g., strain gauges, optical fiber pressure sensors, resistive pressure sensors, semiconductor pressure sensors and other sensors, which detect the pressure exerted by the body onto the supports 106. In examples, sensors 302 detect at least one marker disposed proximate to an area of interest on the body. In an example, the marker includes a magnetic marker, inductive marker, radio RF marker, IR marker or other type of marker to identifies a portion of the body that is to benefit from the method. Sensor interface 320 conditions the data received from sensors 302 and forwards the conditioned data to processor 310. In an example, the at least one marker may be attached to the body via an adhesive or a bandage, or may be affixed to a surface beneath the body.

In an example, an interface 322 receives commands from processor 308 to extend or contract at least one of supports 106 and forwards the commands to the electro mechanic mechanism 324 to extend or contract at least one support 106, so as to modify the pressure exerted locally on the skin by the at least one support 106.

As presented above, controllers 112 and 306 include processors 308 and 310, respectively, which implement or execute machine readable instructions stored in computer readable mediums 312 and 314 to perform some or all of the methods, functions and other processes described herein.

In an example, controllers 112 and 306 include multiple components, e.g., a display device and an interface to an external system. At least one of controllers 112 and 306 provides storage, reporting, and display functions. Information provided by sensors 302, and any information regarding the determined adjustment made to supports 106, including the date and time of the adjustment, may be presented to a user, an administrator for example.

FIG. 4a depicts an array of supports 106 with padding 402 disposed on the top of each support 106. The array of supports 106, with padding 402 disposed thereon is covered by conformal cover sheet 110 that in at least one example, fits snug over the entirely of array of supports 106, forming a recess 404 between adjacent supports 106. Conformal cover sheet 110 protects the supports 106 from moisture, fungus, dust, corrosion, abrasion, and other environmental stresses. Conformal cover sheet 110 may be periodically replaced and laundered to maintain proper patient hygiene.

A lift sheet stretcher 406 is disposed between a plurality of supports 106 within the recess 404 formed by the conformal cover sheet 110. When not in use, lift sheet stretcher 406 is disposed near base 408. Lift sheet stretcher 406 is operable under control of the control system to lift selected portions of the patient above the array of supports 106, via a hoist mechanism (not shown) in order to allow for examination of at least a selected portion of the patient or to replace the conformal cover sheet 110 with minimal stress to the patient (see FIG. 6). In an example, lift sheet stretcher 406 includes horizontal members extending in an X direction and a Z direction between the supports 106. In another example, stretcher 406 is formed from members extending in a single direction, e.g., across a width of base 408.

FIG. 4b shows an example of the array of supports 106 that delivers pressure uniformity and reduces an opportunity for debris to accumulate between supports 106. In FIG. 4b, oversized paddings 408 are deformable to create a continuous top surface 412 when all supports 106 are fully extended to a pre-adjusted state. To replace conformal cover sheet 110 in FIG. 4b, the lift sheet stretcher 406 is raised above the paddings 402, temporarily deforming padding 410 in order to allow the lift sheet stretcher 406 to pass between oversized paddings 410.

FIGS. 5a and 5b depict an example in which a body is disposed on an upper surface of the array of supports 106. An area of concern 502, e.g., an area of an existing lesion, is selected and marked, e.g., areas B, C, and D, with at least one marker 506. In one example, marker 506 includes a trace of a magnetic ink pen. In another example marker 506 includes a trace of a visible or fluorescent ink pen. In an example, sensors 302 include a marker sensor 508, for example a Hall sensor for each support 106, for detecting proximity of the marker sensor 508 to magnetic ink traces of marker 506. Markers 506 may also be inductive markers, IR, optic or RF tags placed on the skin by adhesive tape, or other markers. The marker sensors 508 are monitored by sensor interface 320 that provides sensor data to controller 112. Based upon the sensor data, controller 112 determines which support(s) 106 need to be contracted to reduce pressure on the area of concern 502. As depicted in FIG. 5b, supports 106, corresponding to areas B, C, and D, are contracted by operation of an electro mechanic mechanism 324 under control of interface 322 and controller 112.

As depicted in FIG. 5*b*, a recess 510 is created underneath the patient in areas B, C, and D, by contracting one or more supports 106 to enable the monitoring and/or treating of skin surface 512 with minimal discomfort to the patient.

In an example, FIGS. 6*a* and 6*b* depict an example in which a patient, having a lesion 602, is raised above supports 106 by a lifting force 514 applied to lift sheet stretcher 406.

In situations in which the patient is largely immobile, such as intensive care units (ICUs) or bariatric wards, FIG. 7 depicts a three-dimensional targeting assembly 702 that includes an x-y-z Cartesian robot 704 to deliver one or more sensors/actuators 706, such as miniature cameras 708, humidity/Ph/temperature sensors 710, and sample collectors 712, anywhere on the skin surface 512. Robot 704 includes an X arm 714, a Y arm 716, and a Z arm 718. XY actuator 720 and Z actuator 722, which operate under control of controller 112, position the one or more sensors and actuators to a position corresponding to a selected area of the body.

Figure 8:
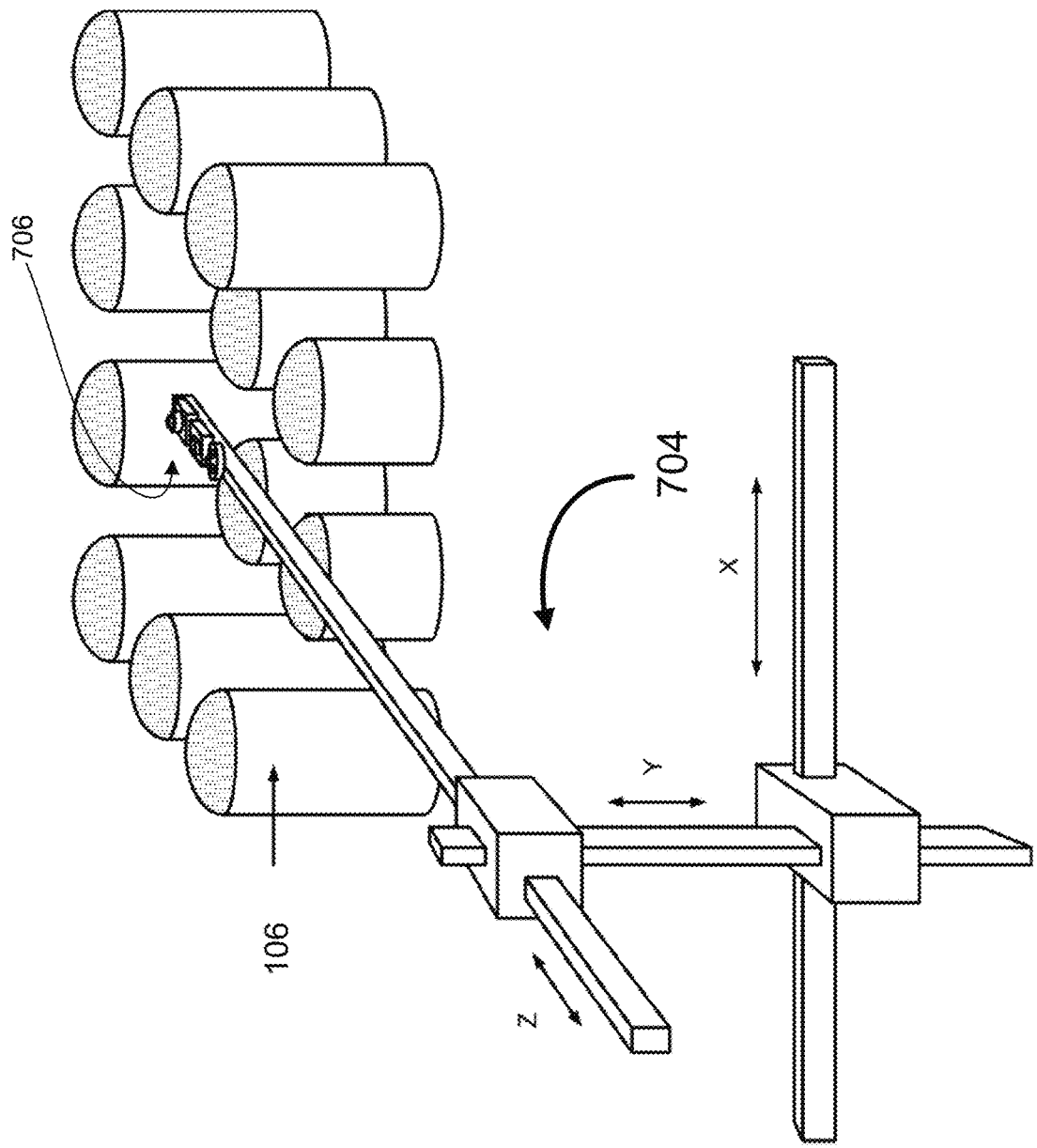

FIG. 8 depicts an example in which access to a targeted area is achieved by robot 704 directing the one or more sensors/actuators 706 through channels formed in-between rows or columns of supports 106, or through paths created by contracting selected supports 106.

Figure 9A:
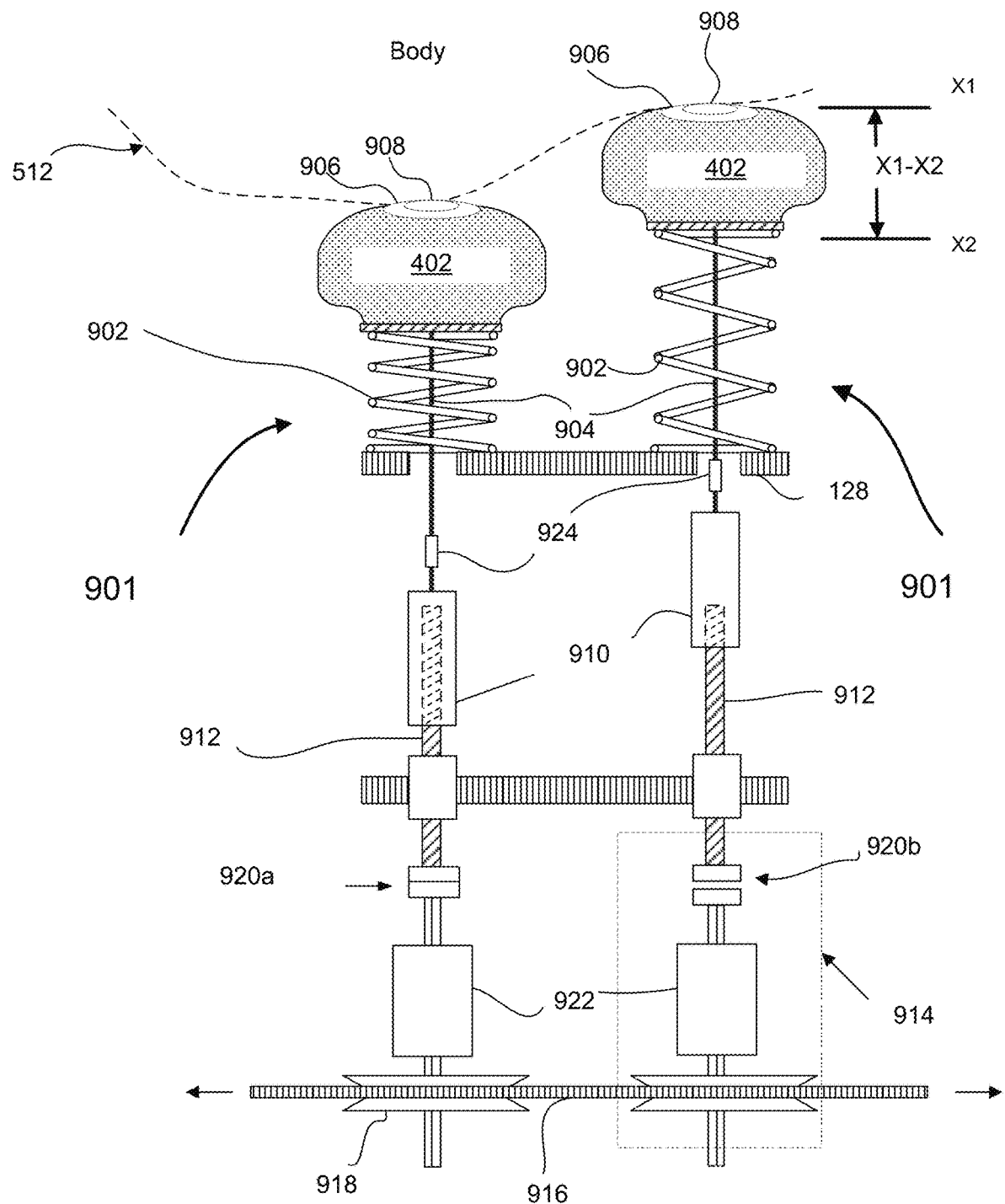
FIGS. 9a and 9b illustrate programmable supports according to an example of the present disclosure.

FIG. 9*a* depicts a mechanism to adjust the length of supports 901. A bottom surface of padding 402 is mounted to a coil spring 902. Coil spring 902 may be composed of a metallic or composite material having a predetermined spring constant K. Compressing coil spring 902 acts to lower the height of the connected padding 402 away from the skin surface 512, while relaxing the tension in coil spring 902 acts to raise padding 402 towards skin surface 512. In an example, the mechanism to compress coil spring 902 includes a cable 904 connecting the base of padding 402 to threaded coupling 910. Cable 904 allows coil spring 902 to compress beyond the programmed adjustment when an impulse force is applied to the padding 402, e.g., in the event a person jumps on the surface of the supports 901. Strain gauge 924 measures the tension (T) in cable 904 and is operable to transmit a measurement of the tension in each support 106 to controller 112.

Supports 901 are operable to be extended (relaxed) or contracted (compressed), in response to commands given by controllers 112 or 306. Supports 901 are pre-compressed such that absent an external force being applied to the supports 901, the tension in cable 904 is equal to a force equal to KX, where K is a predetermined spring constant for supports 106, and X is the displacement, X1−X2, from a known relaxed spring position, X1, to pre-compressed position X2.

FIG. 9*a* further depicts a state in which a body of a patient, or other object, applies pressure to the supports 901. Although supports 901 may marginally or temporarily be compressed due to an added force, e.g., a patient bearing down on the supports 901, the supports 901 are operable to extend or contract due to the added force under control of controller 112. When an object is placed on the supports 901, the force resulting from the applied pressure is equal to:

$$F=PA$$

where P is the pressure applied onto supports 901, and A is a contact area 906 between the body and a particular support of supports 901 being observed. At equilibrium, when the measured tension T and the applied force F balance out the spring force KX, such that:

$$T+F=KX$$

Given that F=PA and K, X and A are known, pressure P can be calculated to be:

$$P=(KX-T)/A$$

Controller 112 monitors pressure P for supports 901 and automatically controls the extension and contraction of each support 901 based on measured pressure P and a predetermined protocol. In an example, contact area 906 includes a pressure sensor 908 to detect the pressure exerted by the body onto the supports 901. Pressure sensor 908 may include resistive pressure sensors, semiconductor pressure sensors as well as other types of sensors.

Threaded coupling 910 is non-rotating and includes a threaded bore to engage threaded shaft 912. Threaded coupling 910 is non-rotating and rotation of threaded shaft 912 operates to either raise or lower threaded coupling 910. In an example, as threaded shaft 912 rotates clockwise to draw threaded coupling 910 downward, padding 402 is pulled down by the attached cable 904 compressing coil spring 902. Conversely, when threaded shaft 912 rotates counter-clockwise, tension on coil spring 902 is relaxed, causing padding 402 to rise towards skin surface 512.

In an example, mechanism 914 is an electro mechanic mechanism 914. Threaded shaft 912 is rotatably mounted to the electro mechanic mechanism 914 along an axis of rotation coinciding with a center of coil spring 902 and padding 402. Mechanism 914 includes clutch controller 922 and friction surfaces 920*a* and 920*b* to transfer a rotational force generated by transmission belt 916 and flywheel 918. FIG. 9*a* depicts friction surfaces 920*a* engaged to transfer a rotational force to threaded shaft 912, and friction surfaces 920*b* are depicted as not engaged to maintain a desired adjustment.

In operation, the rotational force transferred from the mechanism 914 to threaded shaft 912 alternates between clockwise and counter-clockwise cycles to provide the force needed to compress and extend the supports 106. The extent to which supports 901 are extended or contracted is determined by an amount of time each individual mechanism 914 is activated. A strain gauge 924 or equivalent device is disposed between cable 904 and padding 402 to measure tension in cable 904, which is directly related to the pressure exerted by the body on the support 901.

Figure 9B:
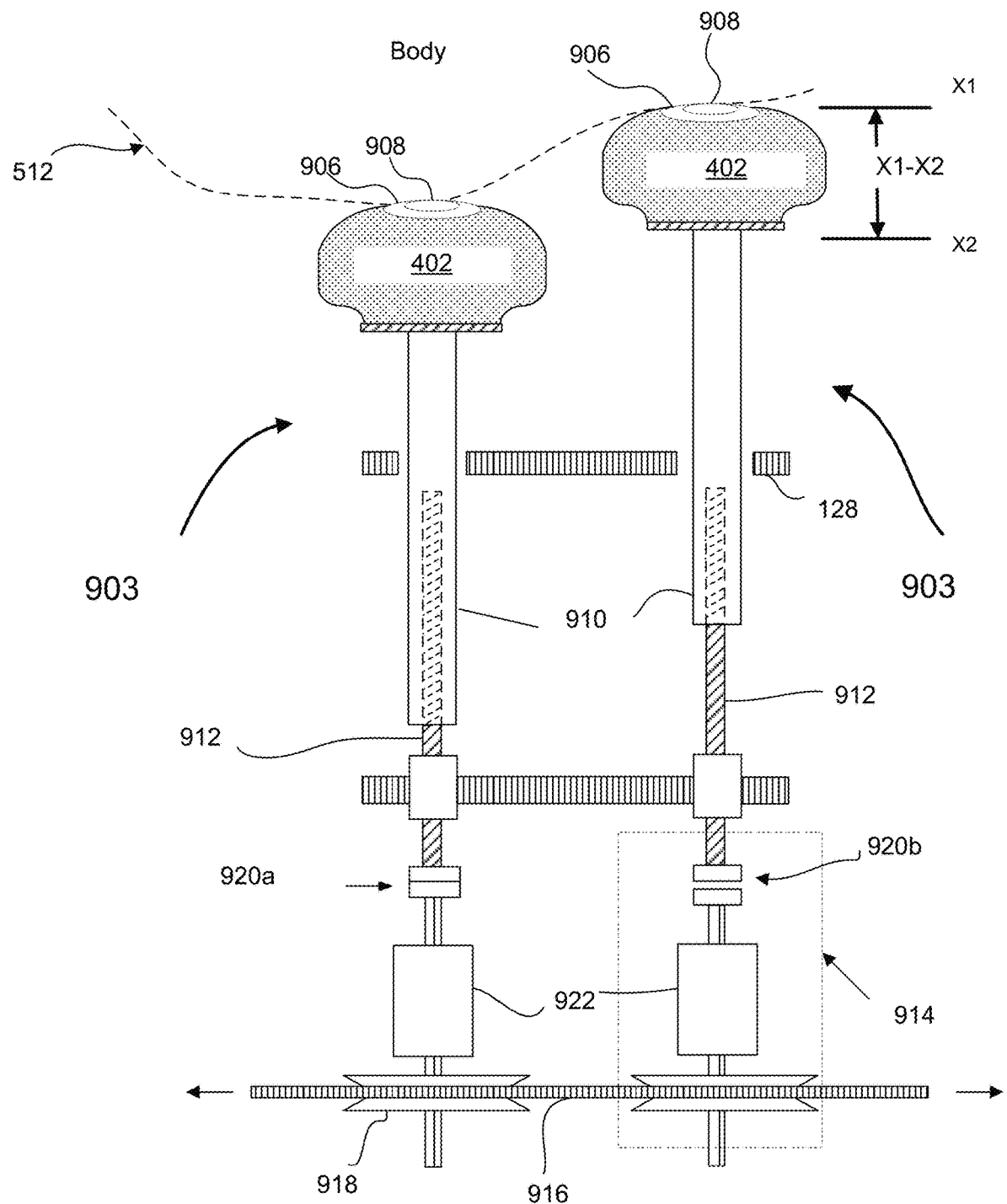

FIG. 9*b* depicts another arrangement of supports 903 where the threaded coupling 910 directly raises padding 402 of the supports 1903. Unlike the supports 901 depicted in FIG. 9*a*, supports 903 do not include a spring supporting padding 402.

Figure 10:
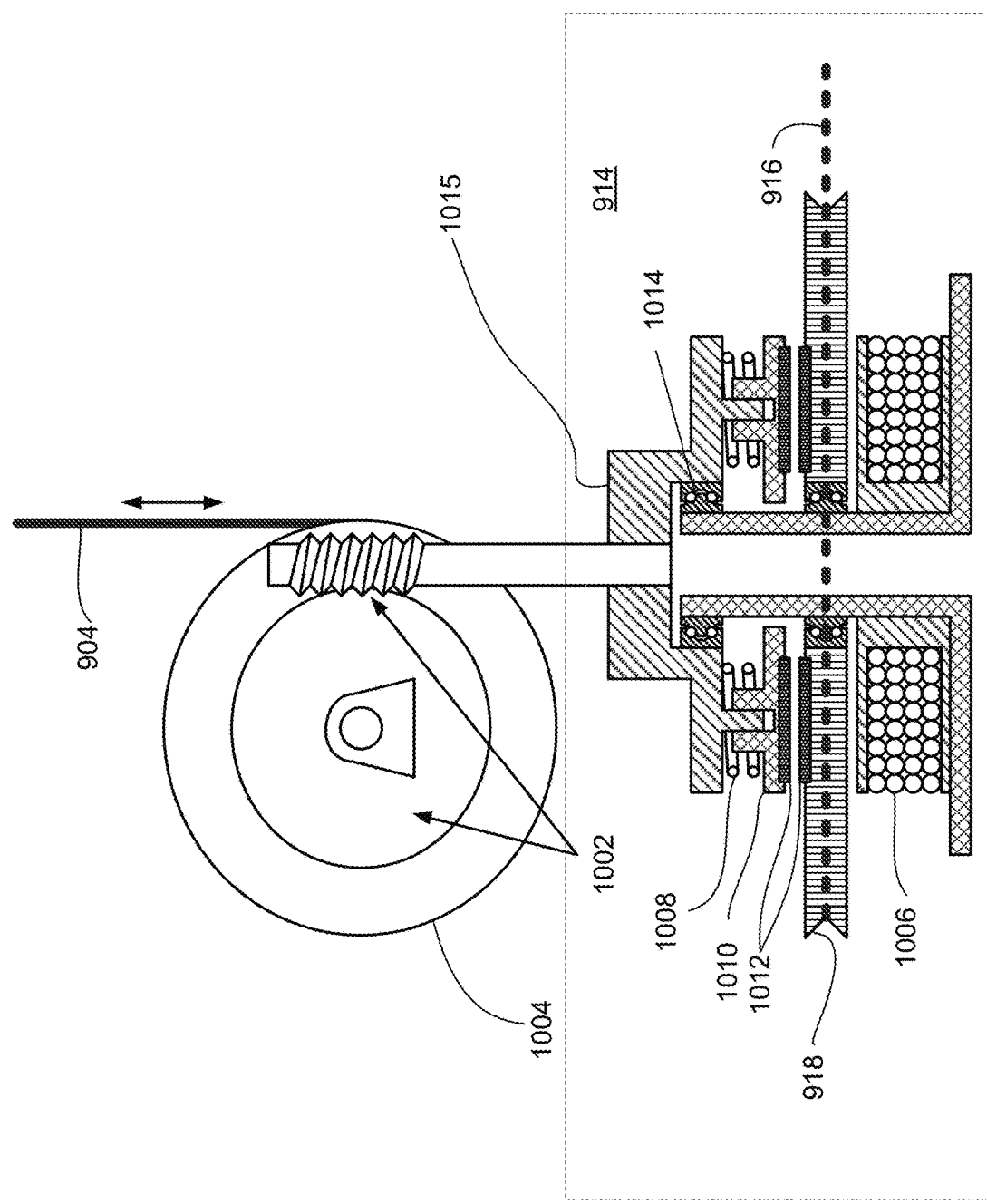
FIG. 10 illustrates a clutch mechanism adjusting a programmable support, according to an example of the present disclosure.

FIG. 10 depicts an example in which supports 901 are adjusted using a cable reel 1004 to either take up or release cable 904. Mechanism 914 rotates worm gear assembly 1002 causing cable reel 1004 to rotate. Reel 1004 is counterbalanced by a spring and is operable to either take-up or release cable 904. Similar in function to cable 904 in FIG. 9*a*, movement of cable 904 acts to either contract or extend support 901. Tension in cable 904 may be measured using a strain gauge 924, as shown in FIG. 9*a*. The measured tension is directly related to the pressure exerted by the object disposed on the supports 901.

Figure 11:
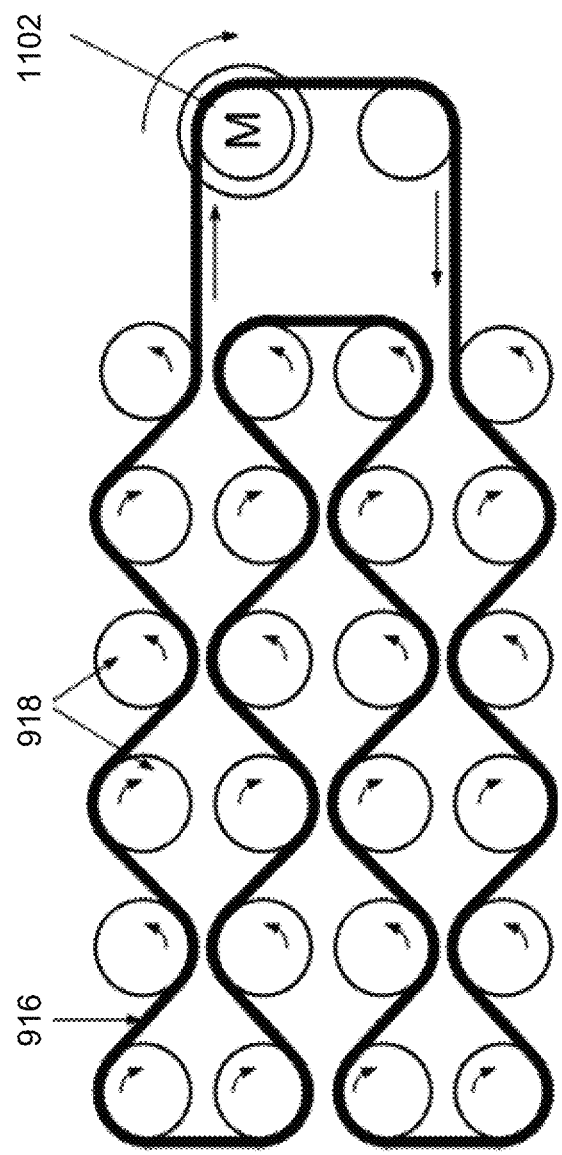
FIG. 11 illustrates a drive mechanism for the programmable supports depicted in the system of FIG. 1, according to an example of the present disclosure.

FIG. 11 depicts a drive mechanism to operate an array of the mechanisms 914 shown in FIGS. 9*a*, 9*b*, and 10. As shown, a computer controlled motor 1102 and drive distribution system operates to drive a transmission belt 916 that engages a number of flywheels 918. In an example, a number of flywheels 918 engaged by motor 1102 is equal to a number of supports 106 in a panel 150 of frame 108. As depicted in FIGS. 9a, 9b, and 10, each flywheel 918 is part of the mechanism 914 operable to adjust each support 901 and 903.

Referring to FIG. 10, a coil 1006 of a selected support, e.g., support 901 of FIG. 9a or support 903 of FIG. 9b, is energized to mechanically couple worm gear assembly 1002 to flywheel 918 and rotate reel 1004 in a clockwise or counter clockwise direction. When coil 1006 is energized, coil 1006 operates against clutch spring 1008 to attract ferromagnetic clutch disk 1010 towards the flywheel 918, bringing corresponding friction surfaces 1012 into contact with each other. Clutch disk 1010 is mechanically connected to worm gear driver 1015, which rotates around a central post supported by bearing 1014. Motor 1102 is operable to rotate in either a forward or reverse direction. Thus by engaging the mechanism 914, support 106 may be either contracted or extended. The extent to which supports 901, 903 are contracted or extended is determined by a length of time each of the individual mechanisms 914 is activated.

Figure 12:
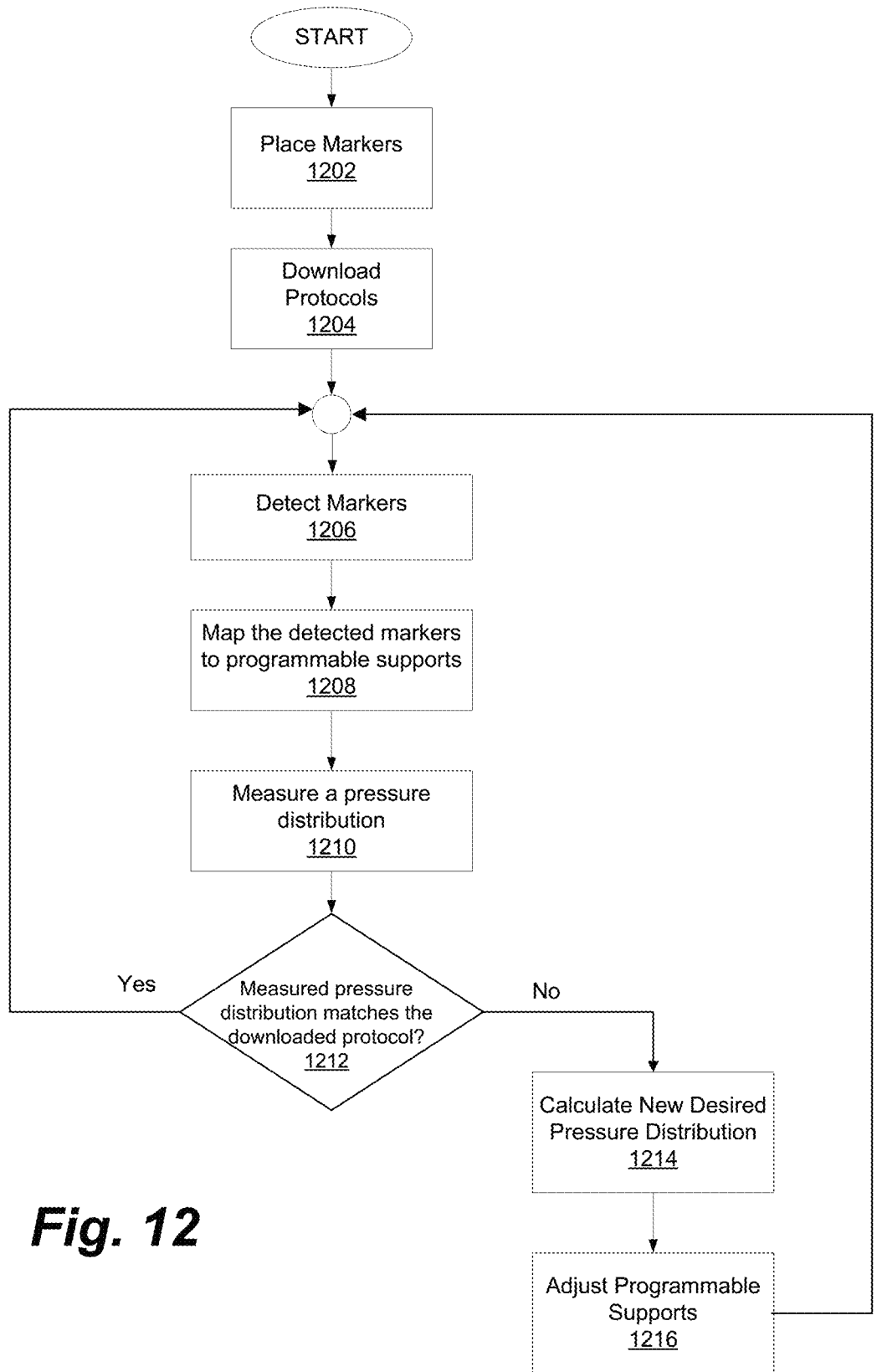
FIG. 12 illustrates a flowchart depicting an operation of the system of FIG. 1 to reduce pressure on areas of interest on the body, according to an example of the present disclosure.

FIG. 12 depicts a flowchart of a method to reduce the pressure exerted upon an identified area of a patient resting atop of a support surface equipped with the array of supports 106.

At block 1202, markers 35 are disposed on the skin surface of a patient to identify portions of the skin surface of the patient to be monitored and to have the benefit of the pressure relieving aspects of the system 100.

At block 1204, protocols are downloaded to at least one of controllers 306 and 112. In an example, the protocols identify a pressure distribution for the patient and in an example include a target pressure distribution for each of the identified portions. In an example, the protocols include a mapping of the supports 106 to predetermined zones, each of the zones having its own predetermined protocol. In an example, the protocols further instruct the controller 112 to automatically adjust the supports 106 such that the pressure applied to the surface of the patient is based on a predetermined schedule.

At block 1208, controller 112 determines the location of the identified area of the body by detecting the position of the markers 506 placed at block 1202. The detection of the position of the markers 506 is performed by measuring signals generated by the marker sensors 508 depicted in FIG. 5. In an example, marker sensors 508 include one or more Hall sensors, resonant sensors, or other types of sensors capable of detecting the markers 506. In an example a marker sensor 508 is disposed on or near each support 106.

At block 1208, controller 112 maps the detected markers 506 to predetermined supports 106.

At block 1210, controller 112 measures a pressure distribution of the patient's body on the padding 402 of supports 106 by determining the pressure exerted by each support 106 on a corresponding section of the patient's body lying thereon. In the example depicted in FIG. 9a, the pressure may be determined by measuring the tension T in the cable 904 and calculating the pressure P using the formula P=(KX−T)/A.

At block 1212, controller 112 determines whether the measured pressure distribution matches a predetermined pressure distribution stipulated by the protocols downloaded at block 1204. In response to a determination that the measured pressure distribution matches the protocol, supports 106 are not adjusted and monitoring is resumed at block 1206.

In response to a determination that the measured pressure distribution for the determined location does not match the protocol, the process continues at block 1214. The measured pressure distribution may not match the protocol for reasons including a movement of the patient and/or an adjustment in the configuration of the panels 150. Movement by/of the patient, or an adjustment in the configuration of the panels 150, may result in the occurrence of new high pressure areas on the skin or in the movement of the markers 506.

At block 1214, a new target pressure distribution may be calculated based upon the protocol, the measured position of the markers 506 by marker sensors 508 and the measured pressure distribution.

At block 1216, the supports 106 may be adjusted by either contracting or extending the supports 106 in accordance with the new target pressure distribution by engaging the corresponding mechanism 914 for a predetermined amount of time.

Figures 13A, 13B:
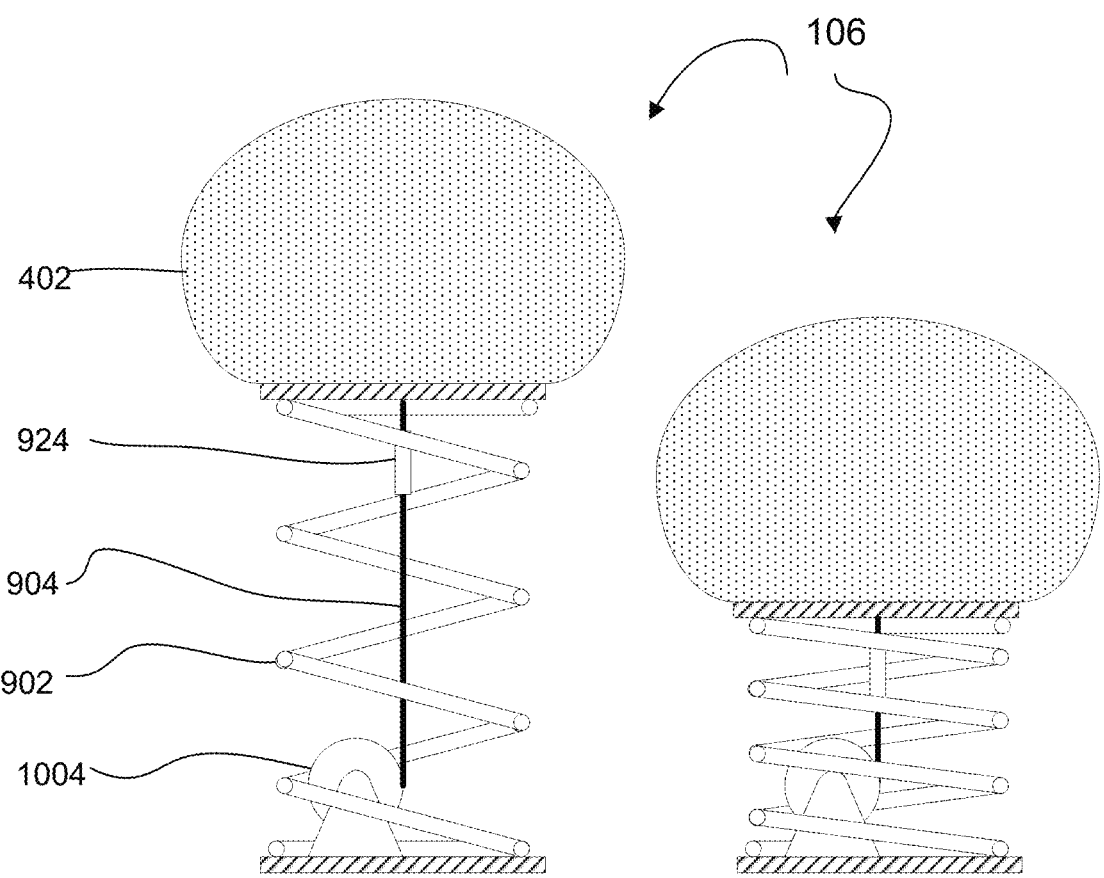
FIGS. 13a and 13b illustrate a programmable support that includes a reel and cable mechanism according to an example of the present disclosure.

FIG. 13 depicts a support 106 in which coil spring 902 is compressed by a motor (not shown) that turns a cable reel 1004 that stores cable 904. Strain gauge 924 measures the tension in cable 904 and indirectly, the pressure exerted by the padding 402 onto a body of the user resting on the support 106. In an example, tension in cable 904 is measured using strain gauge 924. The measured tension is directly related to the pressure exerted by an object apply pressure on the supports 106.

FIG. 14 depicts another example of a programmable support 1400 that includes a roller 1404 that further includes a channel to engage a portion of a coil spring 1402. A driver assembly 1406 urges the roller 1404 in a direction along a circumference of the spring. Rotation of the driver assembly 1406, by a motor (not shown), causes the roller 1404 to compress the coil spring 1402 below the roller 1404, from the bottom of the coil spring 1402 upward. Programmable support 1400 is compact and does not include a cable that may become entangled if an unexpected force higher than a spring reaction force is applied to the programmable support 1400.

Figure 15:
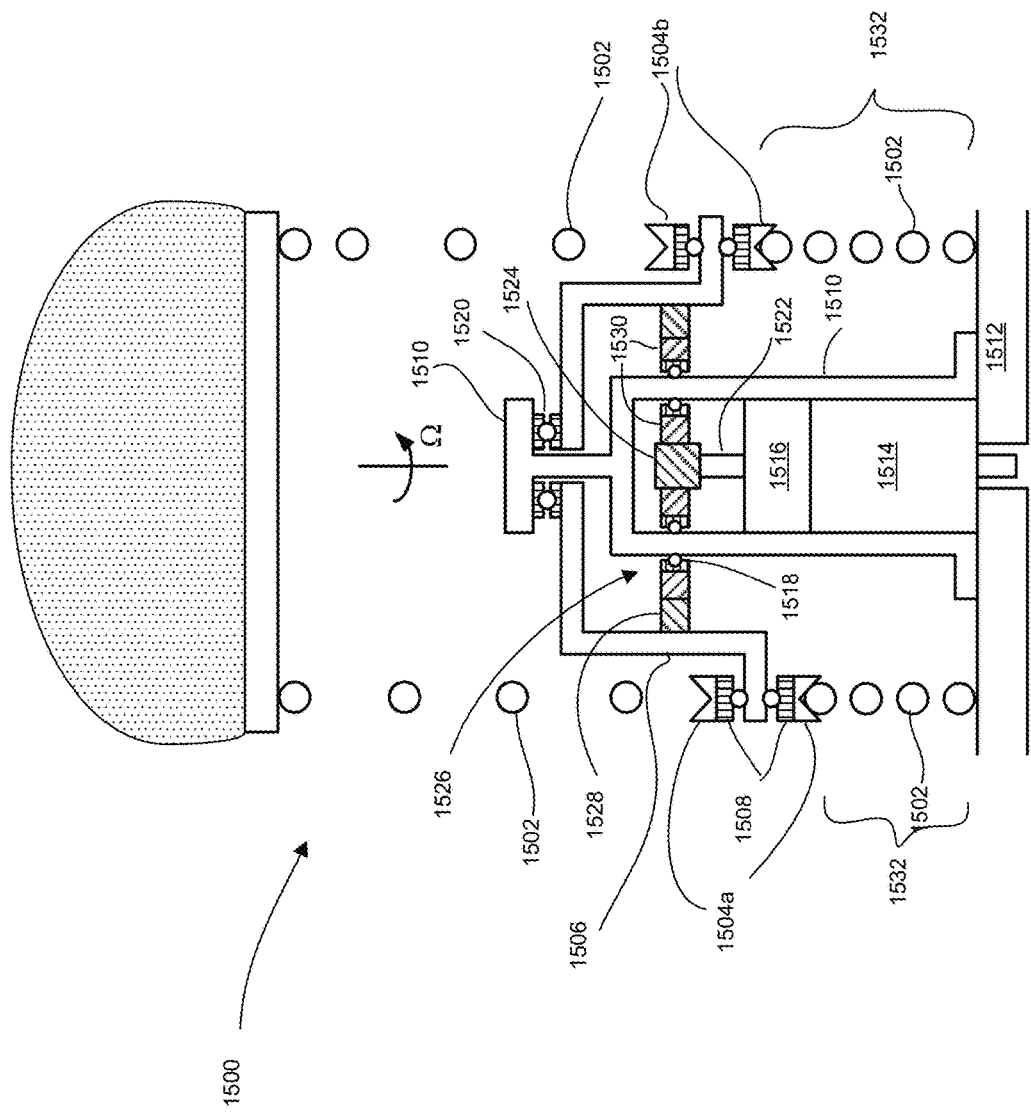
FIG. 15 illustrates a programmable support that includes a motor according to an example of the present disclosure.

FIG. 15 depicts another example of a programmable support 1500 that includes a coil spring 1502. In an example two rollers 1504a and 1504b are opposite and vertically shifted from each other. In a manner similar to the single roller example depicted in FIG. 14, a bottom portion 1532 of coil spring 1502 is compressed by rollers 1504 revolving around an axis of the coil spring 1502. A spring folding force is distributed between the two rollers 1504a and 1504b.

Different quantities and arrangements of rollers, rails, shoes and equivalent devices may be used to fold the coil spring 1502. The rollers 1504a and 1504b are driven by a driver assembly 1506 through roller bearings 1508. A support structure 1510 is fastened to support plate 1512 and mechanically supports motor 1514 and speed reducer 1516.

The support structure 1510 further accommodates roller bearings 1518 and thrust bearing 1520, which connect the support structure 1510 to the driver assembly 1506. In operation, a shaft 1522 of the speed reducer 1516 rotates sun gear 1524 of a planetary gear system 1526 which has ring gear 1528 fastened to the driver assembly 1506. Axis of planet gears 1530 are affixed to the support structure 1510. The sun gear 1524 rotates the planet gears 1530, which in turn rotate the ring gear 1528 and the attached driver assembly 1506 at a higher torque and proportionally lower angular speed than the shaft 1522 of the speed reducer 1516. A force exerted by a compressed bottom portion 1532 of the coil spring 1502 on the rollers 1504 and driver assembly 1506 is balanced by a force exerted by the support structure 1510, through the thrust bearing 1520, onto the driver assembly 1506. Other combinations of elements may be incorporated to achieve similar outcomes.

Figure 16:
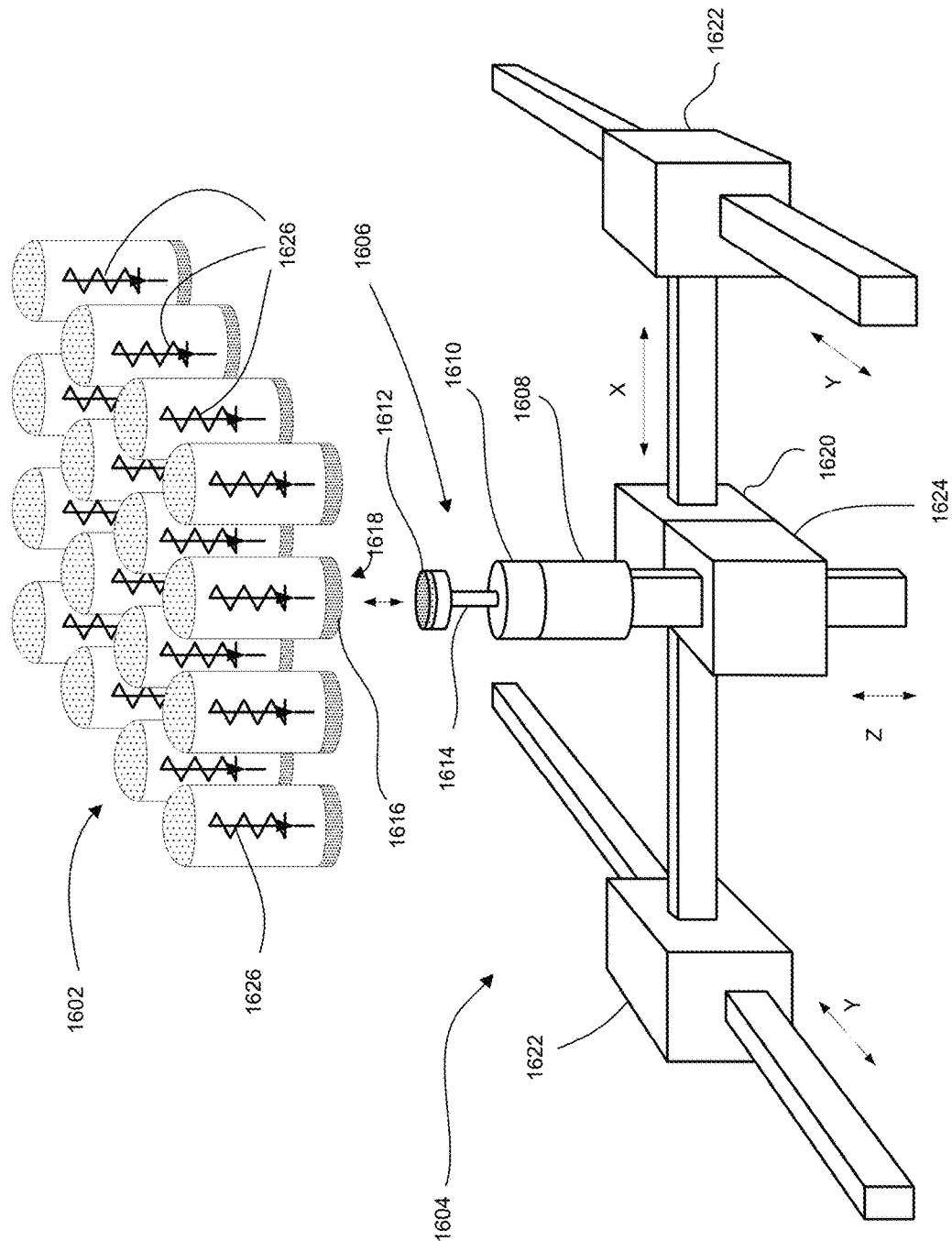
FIG. 16 illustrates a positioning mechanism to drive a programmable support according to an example.

FIG. 16 depicts a robot mechanism 1604 that includes a three dimensional positioning mechanism to position a programmable support adjusting assembly 1606 beneath a selected support 1618 of an array of supports 1602, eliminating the use of individual motors for each support 1602. The three dimensional positioning mechanism includes positioning assembly drivers 1620 (x axis), 1622 (y axis), and 1624 (z axis).

In an example, the robot mechanism 1604 includes at least one motor 1608, a speed reducer 1610 and a friction disk 1612 positioned on a shaft 1614 of the speed reducer 1610. The robot mechanism 1604 positions the friction disk 1612 in contact with a friction disk 1616 of the selected support 1618. Under control of a controller (not shown) the motor 1608 causes a rotation of friction disks 1612 and 1616, which adjusts a length of support 1618.

Figure 17C:
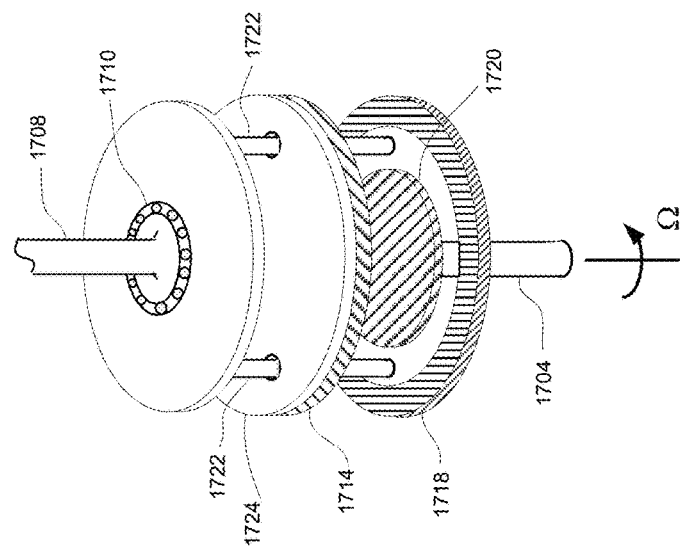
FIGS. 17a-17c illustrate an engagement mechanism according to an example.
Figure 17B:
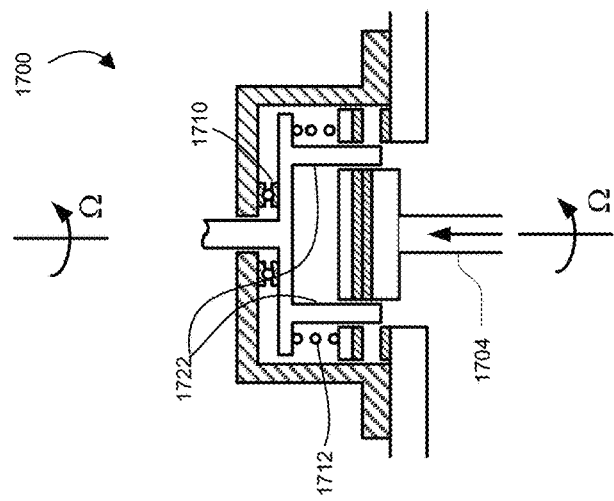
Figure 17A:
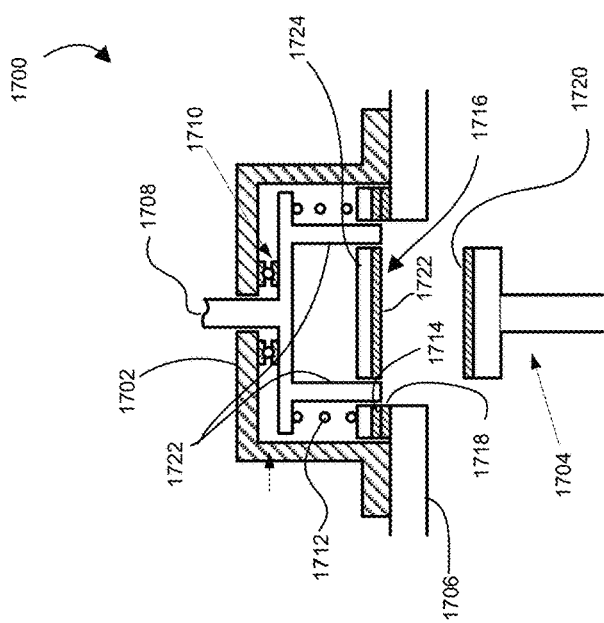

Because motor 1608 only applies torque to a selected support 1618 of supports 1602, springs 1626 of the supports 1602 that are not selected may relax to an uncompressed state, or to a state determined by an external force applied to the unselected supports 1602. FIGS. 17a-17c depicts an engagement mechanism 1700 that prevents a relaxing of a compressed spring 1626 when not being urged by operation of motor 1608.

Engagement mechanism 1700 includes an enclosure 1702 and a drive assembly 1704. Enclosure 1702 is fastened to a support plate 1706. An upper end of spring 1712 urges an output assembly 1708 against the enclosure 1702 through a thrust bearing 1710. A lower end of spring 1712 urges an outer annulus 1714 of a friction disk 1716 towards a friction ring 1718 disposed on the support plate 1706. Friction disk 1716 is structurally supported by support plate 1724. A central portion 1722 of the friction disk 1716 is operable to engage a friction disk 1720 mounted on the drive assembly 1704.

FIG. 17a depicts engagement mechanism 1700 when the central portion 1722 of the friction disk 1716 is not engaged by drive assembly 1704. Because drive assembly 1704 is not acting to compress spring 1712, spring 1712 is relaxed and an upper portion of spring 1712 urges the output assembly 1708 through thrust bearing 1710 and against the enclosure 1702, while the lower portion of spring 1712 urges the support plate 1724 and the attached outer annulus 1714 of the friction disk 1716 against friction ring 1718 fastened to the support plate 1706. The interaction between the outer annulus 1714 of friction disk 1716 and the friction ring 1718 arrests any possible rotation of the output assembly 1708 induced by an unrestrained spring 1626. Output assembly 1708 includes engagement pins 1722 that pass through holes in the support plate 1724 and the friction disk 1716.

FIG. 17b depicts the output assembly 1708 of engagement mechanism 1700 being rotated to adjust a selected support 1602. As shown, the friction disk 1720 of drive assembly 1704 is urged against the central portion 1722 of friction disk 1716, compressing spring 1712. Compressing spring 1712 causes the outer annulus 1714 of the friction disk 1716 to disconnect from the friction ring 1718, thereby removing the arresting action of the friction disks. Rotation of the drive assembly 1704 is transmitted to the output assembly 1708 by action of the rotating support plate 1724 in contact with engagement pins 1722.

FIG. 17c depicts a perspective view of selected components of the engagement mechanism 1700.

The methods, functions and other processes described herein may be implemented using machine readable instructions stored on a computer readable medium 312, 314, which may be non-transitory, such as hardware storage devices (e.g., RAM (random access memory), ROM (read only memory), EPROM (erasable, programmable ROM), EEPROM (electrically erasable, programmable ROM), hard drives, and flash memory).

While the apparatus and methods have been described with reference to examples, various modifications to the described examples may be made without departing from the scope of the claimed features.

The invention claimed is:

1. A system to reduce pressure exerted on a selected area of a body, comprising:
   an array of programmable supports, wherein each programmable support of the array of programmable supports includes:
      an adjustable member; and
      a mechanism to adjust a length of the adjustable member;
   at least one sensor to detect an area of interest on the body;
   channels formed within the array of programmable supports;
   a targeting system to position, via the channels, the at least one sensor to detect the area of interest on the body, another sensor, and an actuator at a targeted area of the body; and
   a processor to:
      receive a signal from the at least one sensor;
      determine a location of the area of interest based on the received signal from the at least one sensor;
      identify at least one programmable support, of the array of programmable supports, proximate to the determined location of the area of interest; and
      provide a signal to the mechanism corresponding to the identified at least one programmable support, wherein the signal is to cause the mechanism to adjust the length of the adjustable member of the identified at least one programmable support.

2. The system of claim 1, wherein the processor provides the signal to the mechanism corresponding to the determined at least one programmable support accordingly to a protocol that includes a target pressure distribution, and
   wherein the target pressure distribution includes a mapping of the programmable supports to predetermined zones, each of the zones having a defined protocol, wherein the defined protocol includes instruction to cause the processor to automatically adjust the identified at least one programmable support according to a predetermined schedule.

3. The system of claim 1, further comprising:
   a set of lifting members disposed in a plurality of recesses formed between adjacent programmable supports; and
   a mechanism to raise selected lifting members of the set of members above a top surface of the array of programmable supports.

4. The system of claim 1, wherein the processor is further to:
   calculate a target pressure distribution on the body by the array of programmable supports based on a protocol;
   measure a pressure exerted by each programmable support of the array of programmable supports on a corresponding section of the body;
   determine whether the calculated target pressure distribution matches the measured pressure; and
   in response to a determination that the measured pressure does not match the protocol,
   calculate a new target pressure distribution, and
   adjust the at least one programmable support based on the new target pressure distribution.

5. The system of claim 1, further comprising:
a plurality of flywheels, each flywheel of the plurality of flywheels to selectively engage a programmable support of the array of programmable supports; and
a motor and drive distribution system to rotationally engage the plurality of flywheels.

6. The system of claim 1, wherein the adjustable member comprises a coil spring, and the programmable support further comprises:
at least one roller that includes a channel to engage a portion of the coil spring; and
a driver assembly to urge the at least one roller in a direction tangential to an axis of the spring,
wherein the driver assembly is to cause the roller to compress the coil spring.

7. The system of claim 1, further comprising a robot mechanism disposed beneath the array of programmable supports, the robot mechanism includes a three dimensional positioning mechanism and a programmable support adjusting assembly, wherein the processor is to:
provide a signal to the three dimensional positioning mechanism to position the programmable support adjusting assembly beneath a selected programmable support of the identified at least one programmable supports; and
control the programmable support adjusting assembly beneath the selected programmable support to adjust the length of the adjustable member associated with the selected programmable support.

8. The system of claim 1, further comprising at least one marker disposed proximate to the area of interest on the body, the at least one marker to be detected by the at least one sensor.

9. A method of reducing pressure on a selected area located on a body, comprising:
receiving, by a processor, a signal from at least one sensor detecting the selected area;
determining, by the processor, a position of the selected area based on the received signal from the at least one sensor;
identifying, by the processor, at least one programmable support, of an array of programmable supports, proximate to the determined location of the selected area;
providing, by the processor, a signal to the identified at least one programmable support to adjust a length of an adjustable member associated with the identified at least one programmable support; and
delivering, under control of the processor, at least one of a sensor and actuator to a targeted area through spaces in-between the programmable supports.

10. The method of claim 9, wherein providing the signal to the indented at least one programmable support includes providing the signal accordingly to a protocol that includes a target pressure distribution, and
wherein the target pressure distribution includes a mapping of the programmable supports to predetermined zones, each of the zones having a defined protocol, and
wherein the defined protocol includes instructions that when executed cause the processor to automatically adjust the identified at least one programmable support according to a predetermined schedule.

11. The method of claim 9, further comprising:
raising selected members of a set of members above the array of programmable supports, wherein the set of members is disposed in a plurality of recesses formed between adjacent programmable supports of the array of programmable supports.

12. The method of claim 9, further comprising:
calculating, by the processor, a target pressure distribution on the body by the array of programmable supports based on a protocol;
measuring, by the processor, a pressure exerted by each programmable support of the array of programmable supports on a corresponding section of the body;
determining, by the processor, whether the calculated target pressure distribution matches the measured pressure, the target pressure distribution includes a mapping of the programmable supports to predetermined zones, each of the zones having a defined protocol according to a predetermined schedule; and
in response to determining that the measured pressure does not match the protocol:
calculating, by the processor, a new target pressure distribution; and
adjusting, by the processor, the at least one programmable support based on the new target pressure distribution.

13. The method of claim 9, wherein the adjustable member comprises a coil spring, the programmable support comprises at least one roller that includes a channel to engage a portion of the coil spring, and wherein the method includes:
urging, by the processor, the at least one roller in a direction along a circumference of the coil spring, causing the at least one roller to compress the coil spring.

14. The method of claim 9, further comprising:
positioning a programmable support adjusting assembly beneath a selected programmable support of the identified at least one programmable supports; and
controlling the programmable support adjusting assembly beneath the selected programmable support to adjusting the length of the adjustable member associated with the selected programmable support.

15. The method of claim 9, wherein receiving the signal from at least one sensor further comprising detecting a marker disposed at a location proximate to the selected area located on the body.

16. A non-transitory computer readable medium, comprising instructions executable by a processor, the instructions to cause the processor to:
receive a signal from at least one sensor detecting a selected area on a body;
determine a position of the selected area based on the received signal from the at least one sensor;
identify at least one programmable support, of an array of programmable supports, proximate to the determined location of the selected area;
position a programmable support adjusting assembly beneath a selected programmable support of the identified at least one programmable support; and
provide a signal to the identified at least one programmable support to adjust a length of an adjustable member associated with the identified at least one programmable support.

17. The non-transitory computer readable medium according to claim 16, wherein to provide the signal to the identified at least one programmable support, the instructions are to cause the processor to provide the signal accordingly to a protocol that includes a target pressure distribution,
wherein the target pressure distribution includes a mapping of the programmable supports to predetermined zones, each of the zones having a defined protocol, and wherein the defined protocol includes instructions that when executed cause the processor to automatically adjust the identified at least one programmable support according to a predetermined schedule.

18. The non-transitory computer readable medium according to claim 16, wherein the instructions are to cause the processor to:
raise selected members of a set of lift members above the array of programmable supports, wherein the set of lift members is disposed in a plurality of recesses formed between adjacent programmable supports of the array of programmable supports.

19. The non-transitory computer readable medium according to claim 16, wherein the instructions are to cause the processor to:
calculate a target pressure distribution on the body by the array of programmable supports based on a protocol;
measure a pressure exerted by each programmable support of the array of programmable supports on a corresponding section of the body;
determine whether the calculated target pressure distribution matches the measured pressure; and
in response to a determination that the measured pressure does not match the protocol,
calculate a new target pressure distribution, and
adjust the at least one programmable support based on the new target pressure distribution.

20. The non-transitory computer readable medium according to claim 16, wherein to receive the signal from the at least one sensor, the at least one sensor is to detect a marker disposed proximate to the selected area on the body.

* * * * *